United States Patent
Balss et al.

(10) Patent No.: US 12,422,367 B2
(45) Date of Patent: Sep. 23, 2025

(54) METHODS FOR DETERMINATION OF VIRUS TITER IN A SAMPLE USING RAMAN SPECTROSCOPY

(71) Applicants: JANSSEN BIOTECH, INC., Horsham, PA (US); OHIO STATE INNOVATION FOUNDATION, Columbus, OH (US)

(72) Inventors: Karin M. Balss, Spring House, PA (US); Zachary Schultz, Columbus, OH (US); Courtney J. Morder, Johnstown, PA (US)

(73) Assignees: JANSSEN BIOTECH, INC., Horsham, PA (US); OHIO STATE INNOVATION FOUNDATION, Columbus, OH (US)

( * ) Notice: Subject to any disclaimer, the term of this patent is extended or adjusted under 35 U.S.C. 154(b) by 249 days.

(21) Appl. No.: 17/990,887

(22) Filed: Nov. 21, 2022

(65) Prior Publication Data

US 2023/0160829 A1   May 25, 2023

Related U.S. Application Data

(60) Provisional application No. 63/281,441, filed on Nov. 19, 2021.

(51) Int. Cl.
*G01N 21/65* (2006.01)
*G01J 3/44* (2006.01)
(Continued)

(52) U.S. Cl.
CPC .............. *G01N 21/658* (2013.01); *G01J 3/44* (2013.01); *G01N 33/56983* (2013.01); *G01N 2201/1293* (2013.01); *G06F 17/10* (2013.01)

(58) Field of Classification Search
CPC .......... G01N 21/658; G01N 33/56983; G01N 2201/1293; G01N 2201/129; G01J 3/44; G06F 17/10
See application file for complete search history.

(56) References Cited

U.S. PATENT DOCUMENTS

| 5,667,998 A | 9/1997 | Dougherty et al. |
| 2009/0086201 A1* | 4/2009 | Dluhy ............. G01N 33/54373 356/301 |

(Continued)

FOREIGN PATENT DOCUMENTS

| WO | 2020/136376 A1 | 7/2020 |
| WO | 2022/003359 A1 | 1/2022 |

OTHER PUBLICATIONS

Wieboldt, Dick. Understanding Raman Spectrometer Parameters. Jun. 10, 2010. Spectroscopy Supplements. Special Issues—Jun. 1, 2010. SpectroscopyOnline (Year: 2010).*

(Continued)

*Primary Examiner* — Hina F Ayub
*Assistant Examiner* — Kaitlyn E Kidwell
(74) *Attorney, Agent, or Firm* — Troutman Pepper Locke LLP

(57) ABSTRACT

Disclosed is a method of quantifying virus titer in a sample using Raman spectroscopy. This method comprises providing a sample; providing a model for determining viral titer in the sample; irradiating the sample with a light source; and acquiring a Raman spectrum of the sample. The method further involves quantifying the viral titer of the sample by applying a virus component of the Raman spectrum to the model for determining viral titer. Other aspects of the disclosure relate to a method for generating a model suitable for quantifying viral titer in a sample.

26 Claims, 13 Drawing Sheets

Without GFP

With GFP

(51) Int. Cl.
*G01N 33/569* (2006.01)
*G06F 17/10* (2006.01)

(56) References Cited

U.S. PATENT DOCUMENTS

2009/0149344 A1 6/2009 Zhao et al.
2009/0257056 A1 10/2009 Demirel et al.
2012/0071352 A1 3/2012 Liao et al.

OTHER PUBLICATIONS

Fan et al. (2010, Detecting food- and waterborne virus by surface-enhanced raman spectroscopy, J. Food Sci. 75(5):M302) (Year: 2010).*
Rapid and Sensitive Detection of Rotavirus Molecular Signatures Using Surface Enhanced Raman Spectroscopy Driskell JD, Zhu Y, Kirkwood CD, Zhao Y, Dluhy RA, et al. (2010) Rapid and Sensitive Detection of Rotavirus Molecular Signatures Using Surface Enhanced Raman Spectroscopy. PLOS One 5(4): e10222 (Year: 2010).*
Quantitative Serodiagnosis of Scrub Typhus Using Surface-Enhanced Raman Scattering-Based Lateral Flow Assay Platforms Hi Lee, Joonki Hwang, Kihyun Kim, Jinhyeok Jeon, Sangyeop Lee, Juhui Ko, Jichul Lee, Minhee Kang, Doo Ryeon Chung, and Jaebum Choo Analytical Chemistry 2019 91 (19), 12275-12282 (Year: 2019).*
International Search Report and Written Opinion for PCT/US2022/050543 dated Feb. 9, 2023.
Extended European Search Report for European Application No. 22896568.7 (Jan. 23, 2025).
Driskell et al., "Rapid and Sensitive Detection of Rotavirus Molecular Signature Using Surface Enhanced Raman Spectroscopy," Plos One 5(4):e10222 (2010).
Lee et al., "Rapid and Sensitive Determination of HIV-1 Virus Based on Surface Enhanced Raman Spectroscopy," Journal of Biomedical Nanotechnology 11:2223-2230 (2015).
Shanmukh et al., "Rapid and Sensitive Detection of Respiratory Virus Molecular Signatures Using a Silver Nanorod Array SERS Substrate," Nano Letters 6(11):2630-2636 (2006).

* cited by examiner

METHODS FOR DETERMINATION OF VIRUS TITER IN A SAMPLE USING RAMAN SPECTROSCOPY

This application claims the priority benefit of U.S. Provisional Patent Application Ser. No. 63/281,441, filed Nov. 19, 2021, which is hereby incorporated by reference in its entirety.

This invention was made with government support under R01 GM109988 awarded by the National Institutes of Health. The government has certain rights in the invention.

FIELD

The present disclosure relates to methods for determination of virus titer in a sample using Raman spectroscopy.

BACKGROUND

The ability to rapidly identify and determine lentiviral titer is critical to a number of biomedical challenges, from gene editing to pharmaceutical and vaccine development. Lentiviruses are an enveloped virus that have been shown to efficiently deliver genetic information to reprogram cells, which makes them particularly useful in immunotherapies (Kalos et al., "T Cells with Chimeric Antigen Receptors Have Potent Antitumor Effects and Can Establish Memory in Patients with Advanced Leukemia," *Science Translational Medicine* 3(95):95ra73 (2011); Brentjens et al., "Eradication of Systemic B-Cell Tumors by Genetically Targeted Human T Lymphocytes Co-Stimulated by CD80 and Interleukin-15," *Nature Medicine* 9(3):279-286 (2003); Zuffere et al., "Multiply Attenuated Lentiviral Vector Achieves Efficient Gene Delivery In Vivo," *Nat. Biotechnol.* 15(9):871-875 (1997)). When producing these viruses for therapy, the lentiviruses are modified so that they contain the necessary information to modify cells and also prevent replication of the virus to prevent unintended infections (Zuffere et al., "Multiply Attenuated Lentiviral Vector Achieves Efficient Gene Delivery In Vivo," *Nat. Biotechnol.* 15(9):871-875 (1997); Wang et al., "Clinical Manufacturing of CART Cells: Foundation of a Promising Therapy," *Molecular Therapy—Oncolytics* 3:16015 (2016)). This means that each transformed virus can only transform one cell. Therefore, knowing the effective titer of the transformed virus is key to knowing the dose and expectations for therapy.

Current methods of characterizing viruses and determining viral titer include ELISA (Wu et al., "Digital Single Virus Electrochemical Enzyme-Linked Immunoassay for Ultrasensitive H7N9 Avian Influenza Virus Counting," *Analytical Chemistry* 90(3):1683-1690 (2018)), PCR (Carr et al., "Development of a Real-Time RT-PCR for the Detection of Swine-lineage Influenza A (H1N1) Virus Infections," *Journal of Clinical Virology* 45(3):196-199 (2009); Pivert et al., "A First Experience of Transduction for Differentiated HepaRG Cells using Lentiviral Technology," *Scientific Reports* 9(1):12910 (2019)), and cell culture (Gueret et al., "Rapid Titration of Adenoviral Infectivity by Flow Cytometry in Batch Culture of Infected HEK293 Cells," *Cytotechnology* 38(1-3):87-97 (2002)). Although these methods are reliable for detecting and quantifying viruses, there are some disadvantages. These methods often involve infecting a known number of cells and then performing analysis, such as PCR, to determine successful reprogramming. Assays and cell culture can be time consuming when considering incubation times and require considerable sample preparation. This means that these methods can take anywhere from days to weeks to provide results. The ability to quickly characterize these viruses is critical in pharmaceutical and vaccine development.

SERS utilizes plasmonic metallic nanostructures to enhance the Raman signal of an analyte, thus providing a molecular fingerprint based on the analyte's vibrational modes (Kneipp et al., "Ultrasensitive Chemical Analysis by Raman Spectroscopy," *Chemical Reviews* 99(10):2957-2976 (1999); Moskovits, M., "Surface-Enhanced Spectroscopy," *Reviews of Modern Physics* 57(3):783-826 (1985); Stiles et al., "Surface-Enhanced Raman Spectroscopy," *Annual Review of Analytical Chemistry* 1(1):601-626 (2008)). SERS has previously shown the ability to detect virus particles and provide a molecular fingerprint based on the composition of the virus (Shanmukh et al., "Rapid and Sensitive Detection of Respiratory Virus Molecular Signatures Using a Silver Nanorod Array SERS Substrate," *Nano Letters* 6(11):2630-2636 (2006); Lim et al., "Identification of Newly Emerging Influenza Viruses by Surface-Enhanced Raman Spectroscopy," *Analytical Chemistry* 87(23):11652-11659 (2015); Dardir et., "SERS Nanoprobe for Intracellular Monitoring of Viral Mutations," *Journal of Physical Chemistry C* 124(5):3211-3217 (2020); Paul et al., "Bioconjugated Gold Nanoparticle Based SERS Probe for Ultrasensitive Identification of Mosquito-Borne Viruses Using Raman Fingerprinting," *Journal of Physical Chemistry C* 119(41):23669-23675 (2015); Verduin et al., "RNA-Protein Interactions and Secondary Structures of Cowpea Chlorotic Mottle Virus for In Vitro Assembly," *Biochemistry* 23(19):4301-4308 (1984)). Different strains of influenza have been distinguished due to differences in SERS spectra arising from differing surface proteins on the envelope of the virus (Lim et al., "Identification of Newly Emerging Influenza Viruses by Surface-Enhanced Raman Spectroscopy," *Analytical Chemistry* 87(23):11652-11659 (2015)). SERS can also distinguish between adenovirus, HIV, and rhinovirus particles based on signal changes arising from the different nucleic acids and amino acids that compose each virus (Shanmukh et al., "Rapid and Sensitive Detection of Respiratory Virus Molecular Signatures Using a Silver Nanorod Array SERS Substrate," *Nano Letters* 6(11):2630-2636 (2006)). Many SERS studies of viruses involve developing a SERS based assay by functionalizing nanostructures with aptamers (Dardir et., "SERS Nanoprobe for Intracellular Monitoring of Viral Mutations," *Journal of Physical Chemistry C* 124(5):3211-3217 (2020); Negri et al., "Identification of Virulence Determinants in Influenza Viruses," *Analytical Chemistry* 86(14):6911-6917 (2014)) or antibodies (Paul et al., "Bioconjugated Gold Nanoparticle Based SERS Probe for Ultrasensitive Identification of Mosquito-Borne Viruses Using Raman Fingerprinting," *Journal of Physical Chemistry C* 119(41):23669-23675 (2015); Driskell et al., "Low-Level Detection of Viral Pathogens by a Surface-Enhanced Raman Scattering Based Immunoassay," *Analytical Chemistry* 77(19):6147-6154 (2005)) to target the virus.

The present disclosure is directed at overcoming current deficiencies in the determination of virus titer.

SUMMARY

A first aspect of the disclosure is directed to a method of quantifying virus titer in a sample using Raman spectroscopy. This method comprises providing a sample; providing a model for determining viral titer in the sample; irradiating the sample with a light source; and acquiring a Raman spectrum of the sample. The method further involves quantifying the viral titer of the sample by applying a virus component of the Raman spectrum to the model for determining viral titer.

Another aspect of the present disclosure is directed to a method for generating a model suitable for quantifying viral titer in a sample. This method comprises providing two or more samples, each sample containing a known virus type and corresponding titer; subjecting each sample to Raman spectroscopy to produce a reference spectrum for each known virus type and titer; identifying a virus type-specific component from the reference spectra; and determining a score for said component for each sample of known virus type and known titer. The method further involves generating the model for quantifying viral titer based on said scores.

To provide a more straightforward and rapid approach to determining viral titer, the use of SERS was explored. SERS was used to detect and distinguish virus particles in formulation media. Two types of virus particles, one containing an inserted gene and one without that gene, were analyzed at various concentrations. Multivariate curve resolution (MCR) was then used to differentiate the spectra and determine the viral titer of the particles with the inserted gene. This was performed in solution using both silver and gold substrates at different excitation wavelengths. The spectral differences arising from using different substrates and excitation wavelengths was also explored.

As demonstrated in the accompanying Examples, SERS provides a rapid approach to determining viral titer with less sample preparation than current methods. While SERS has already been shown to distinguish between virus types and strains, the methodology described herein allows for the determination of viral titer using direct SERS measurements. While results are presented using lentivirus particles, this same methodology can be applied to other virus types. This technique may also be used to quantify modifications to a viral genome.

BRIEF DESCRIPTION OF THE DRAWINGS

FIG. 5A is a graph showing spectra of 3 component loadings of the model. FIG. 5B is a graph showing scores of each spectra on component 2 plotted against component 3. The scores on component 2 show a relationship with viral titer. FIG. 5C is a graph showing an average score for each concentration plotted against viral titer. FIG. 5D is a bar graph of the average scores on component 2 of the lentivirus particles without GFP (50,000 TU/mL) and the storage media of the particles plotted compared with the average score of the particles with GFP (50,000 TU/mL).

FIG. 8A is a graph showing an average SERS spectra of lentivirus with (grey) and without (black) GFP at 50,000 TU/mL. A 3 component MCR model was developed using all spectra acquired at this concentration. FIG. 8B is a graph showing component loadings of this MCR model. FIG. 8C is a 3-dimensional plot of the scores for each of the three components. Only spectra of particles containing GFP score highly on component 3. FIG. 8D is a graph showing comparison of the component spectra arising from the GFP vector acquired using a silver (black) and gold (grey) substrate.

FIG. 10A is a graph showing an average SERS spectra for difference concentrations of JLV1. FIG. 10B is a 3-dimensional plot of the scores for each of the three components of the JLV1 sample, and FIG. 10C is a graph showing component loadings of this MCR model. FIG. 10D shows the average score for each sample (from $10^3$ to $10^6$ TU/mL) on component 1. FIG. 10E is a calibration curve for determining viral titer of JLV1 over the range of $10^3$ to $10^5$ TU/mL. FIGS. 10F-H are graphs showing comparison of spectra component scores for the JLV1 sample with two components plotted against one another: component 1 versus component 2 (FIG. 10F), component 1 versus component 3 (FIG. 10G), and component 2 versus component 3 (FIG. 10H).

DETAILED DESCRIPTION

Definitions

Figure 1:
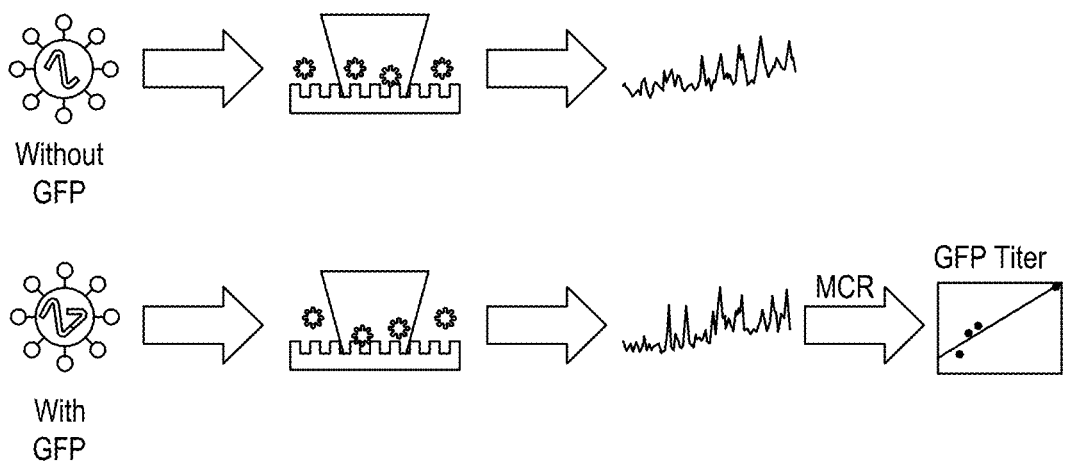
FIG. 1 is a schematic for the experimental setup. Two types of virus particles were analyzed by SERS. One particle contains a vector encoding for green fluorescent protein (GFP) and one does not. SERS spectra were analyzed using multivariate curve resolution (MCR) to determine a component spectrum arising from the GFP vector. This component was then used to determine the viral titer of the GFP-encoding particles.

Before the present methods are described, it is to be understood that this invention is not limited to the particular methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value, or more particularly ±5% of the recited value, or as ±3%, ±2%, or ±1% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Methods of Quantifying Virus Titer in a Sample

A first aspect of the disclosure is directed to a method of quantifying virus titer in a sample using Raman spectroscopy. This method comprises providing a sample and providing a model for determining viral titer in the sample. The sample is irradiated with a light source, and a Raman spectrum of the sample is acquired. The method further involves quantifying the viral titer of the sample by applying a virus component of the Raman spectrum to the model for determining viral titer.

A virus is submicroscopic infectious agent (typically smaller than a bacterium) that is only capable of replicating inside the living cell of another organism. Viruses may have RNA or DNA-based genomes. In accordance with the methods described herein, a virus encompasses any naturally occurring virus, modified virus, or viral vector. Thus, although the viral titer of any wild type virus may be assessed in accordance with the present disclosure, it will be appreciated that the utility of methods disclosed herein extend to the assessment of viral titers of mutant or modified viruses (e.g., viruses comprising one or more nucleic acid substitutions, insertions, deletions or translocations as compared to a wild type or naturally occurring virus, or absent large portions of genetic material encoding for viral proteins) or viral vectors.

Viral titer as determined in accordance with the methods disclosed herein is described in the context of detecting virus particles. A virus particle or viral particle is a virus that is independent from its host (i.e., not found in a cell), but comprises the viral genome and the viral capsid (or outer coat of the virus). The methods described herein are also suitable for determining the titer of virus-like particles. Virus-like particles are small particles that contain certain proteins from the outer coat of a virus, but do not contain any or all of the genetic material from the virus and cannot cause infection. Virus-like particles (VLPs) can be naturally occurring or synthesized by individual expression of virus structural proteins which self-assemble into a virus-like structure. Synthetic virus-like particles can also comprise liposome or polymeric particles modified to display and/or contain virus proteins, e.g., virus structural proteins. For purposes of the present disclosure, when reference is made to determining the titer of a viral particle, it is to be understood that this is encompasses determining the titer of viral particles and all forms of virus-like particles, i.e., naturally occurring VLPs, synthetic VLPs, liposome based VLPs, polymeric particle VLPs, etc.

In some embodiments, the viral titer of the sample is determined in a sample that comprises one or more virus particle types. In some embodiments, the sample contains two or more virus particle types, e.g., two virus particle types, three virus particle types, four virus particle types, five virus particle types, or more than five virus particle types.

In any embodiment, the two or more virus particle types differ by one or more genetic elements. For example, the two or more virus particle types in a sample may differ by one or more genetic insertions, substitutions, translocations, or deletions in the virus particle genome. In some embodiments, the two or more virus particles differ by a genetic insertion, for example, the insertion of an exogenous gene or portion thereof into the virus particle genome. The one or more genetic differences, which may also give rise to one or more protein differences between virus particle types, provides the basis for identifying a virus type-specific components useful for quantifying virus titer as described herein.

The methods disclosed herein are also suitable for determining titer of viral vectors in a sample. Viral vectors are modified, non-infectious versions of a virus commonly used to introduce genetic material into target cells (e.g., genes of therapeutic use). Viral vectors therefore have particular utility, e.g. for gene therapy, cell therapy or for other molecular applications, and their production is central to the gene therapy and cell therapy industries. In some embodiments, the viral titer of the sample is determined in a sample that comprises one or more viral vectors. In some embodiments, the sample contains two or more viral vectors, e.g., two viral vectors, three viral vectors, four viral vectors, five viral vectors, or more than five viral vectors.

In any embodiment, the titer of viral vectors which are produced by packaging cell lines may be monitored or assessed by the methods disclosed herein. It is particularly important in the gene therapy and cell therapy fields to be able to measure produced titer in a sensitive manner, e.g. so that production processes, such as production from a producer cell line, can be accurately monitored and managed. A virus therefore does not need to be fully functional or wild type to be monitored or assessed by the methods disclosed herein.

The term "viral titer" refers to the quantity of virus (i.e., virus particle, VLP, and/or viral vector) present in a given volume. Any type of viral titer may be assessed with the present invention, e.g. physical viral titer, functional viral titer (also referred to as infectious viral titer) or transducing viral titer, may be assessed.

In a particular embodiment, the physical viral titer may be assessed. Physical viral titer is a measure of the concentration of viral particles in a sample and is usually based on the presence of a viral protein or viral nucleic acid, i.e., a virus component. Physical titer may be expressed as viral particles per mL (VP/mL), viral genomes per mL (vg/mL), viral copies per mL, or RNA copies per mL and can be determined using the methods described herein. Physical titer measurements do not always distinguish between empty or defective viral particles and particles capable of infecting a cell. Thus, the physical viral titer can be distinguished from functional titer or infectious titer which determines how many of the particles produced can infect cells, and the transducing viral titer which determines how many of the functional viral particles contain a gene of interest (e.g. for the production of a viral vector, the transducing viral titer may be relevant). Thus, a determination of physical titer is not equivalent to a determination of functional titer, unless all particles in a sample are functional. Indeed, functional titer is often 100 to 1000 fold less than physical titer.

Alternatively, the functional or infectious titer may be measured or assessed with the present invention, where functional or infectious titer is a measure of the amount of viral particles present in a particular volume which are capable of infecting a target cell. Functional titer may be expressed as plaque forming units per mL (pfu/mL), infectious units per mL (ifu/mL), or transfection units per mL (TU/mL).

The transducing titer is a measure of the amount of viral particles present in a particular volume which are capable of infecting a target cell and which comprise a gene of interest. Transducing titer may be expressed as transducing units/mL and may be assessed using the assay described herein. A skilled person will appreciate that functional titer or transducing titer may be determined by scaling down any value obtained for physical titer. As discussed above, the fold differences between physical and functional or transducing titer are well understood in the art. Thus, in one aspect of the invention, functional or transducing titer may be determined indirectly by the methods of the invention (e.g. through scaling down a value obtained for physical titer). The methods of the invention may therefore include an additional step of scaling down a determination of physical titer to determine the functional or transducing titer.

The methods of the invention can monitor or assess viral titer. Thus, the methods of the invention are capable of determining viral titer e.g. levels, amounts or concentration of viral particles present in a sample. Particularly, the methods can thus determine whether levels, amounts or concentration of virus increase or plateau over time (e.g., by assaying a sample at different time points), or vary (e.g., increase, decrease or are equivalent) compared to different samples (e.g., assayed at the same or equivalent time point). In this way, the methods disclosed herein can be used for example, to assess the efficiency of a production method of the virus, e.g., where the detection or determination of a high level of virus may be indicative of an efficient method and a low level of virus may be indicative of a sub-optimal production method, or can be used to determine the importance of particular factors in the production method of the virus, e.g., by comparison with viral titers measured during other modified production methods (for the same or different virus).

The methods of the invention can also be used to assess any process downstream of the viral production process, e.g., to determine whether any such process has affected viral titer. In any embodiment, the methods disclosed herein are suitable for assessing purification methods which may be employed to determine whether such purification methods have had any impact on titer, e.g., whether titer has increased, decreased or remained equivalent after such a purification as compared to the viral titer which was present in the sample before purification. The methods disclosed herein may further be used to assess large scale manufacture of virus, e.g., of virus particles, VLPs, or viral vectors, which may be particularly important for the manufacture of viral particles or vectors for gene therapy.

The methods disclosed herein are capable of determining an increase or decrease in viral titer of a sample relative to another sample. In any embodiment, the methods disclosed here are suitable for determining an increase of about 1%, 5%, 10%, 20%, 30%, 40%, 50%, 60%, 70%, 80% or 90% of the viral titer as to which a measurement is being compared, and a decrease in viral titer of about 1%, 5%, 10%, 20%, 30%, 40%, 50%, 60%, 70%, 80%, or 90% of the viral titer as to which a measurement is being compared. An equivalent viral titer may be within 5% of the viral titer to which a measurement is being compared.

In this regard, it will be appreciated that for some purposes, it may be desirable to assess viral titer prior to carrying out a method and as well as after and/or during a method, in order to determine whether any change or variation in the viral titer has occurred. The methods disclosed herein may further include a step of comparison of viral titer, e.g. with the viral titer within a different sample (at an equivalent or different time point), or within the same sample at a different point in time. In another embodiment, the methods may be used to determine the extent of viral infection in a subject, e.g. to determine whether an infection is being successfully treated or reduced. In such a method, it may be desirable to compare the viral titer in a sample, e.g., a sample of the same type from a subject at different time points, to determine whether the viral titer increases, decreases or remains equivalent over time. Alternatively, or additionally, it may be desirable to compare the viral titer in a sample from an individual with viral titer measurements which have been previously obtained for a condition and which for example may be indicative of the stage of infection and/or the prognosis.

Alternatively, the methods disclosed herein may not determine an actual amount, level or concentration of a virus in a sample, but may determine whether the amount, level or concentration is above or below an acceptable threshold, e.g., for a production method, the threshold may determine whether there is an acceptable level of viral particles within a sample. The methods disclosed herein may determine whether levels of viral titer are increased, decreased, or comparable to those of a previously assayed sample, and thus it will be appreciated that for particular applications, it may not be necessary to determine the actual viral titer (e.g., amount or concentration of virus present).

In accordance with the methods of determining viral titer in a sample as described herein, a suitable sample includes any sample which contains or is expected to contain one or more virus particles, VLPs or viral vectors. Viral titer in the sample may be measured by Raman spectroscopy in real-time, in situ, or may be carried out on samples ex situ.

By "in situ" it is meant that measurements to obtain the intensities of Raman scattered light in a culture capable of producing virus particles are taken from the primary culturing environment in which the virus particles are produced, and not from a sample extracted from the primary culturing environment. Thus, by taking measurements "in situ" there are no requirements for liquid handling steps. Thus, removal of a sample from its environment may not be necessary for particular applications of the present invention, and in situ measuring of a sample may be preferred. An in situ measurement of a sample may allow for regular assessment of viral titer in a sample without the need for an actual sampling step, where a portion of sample is removed. Viral titer assessment in this respect can be measured accurately and sensitively in real time without the need for additional steps which could introduce cost and error.

Alternatively, the methods disclosed herein may be carried out on samples ex situ. By "ex situ" it is meant that measurements to obtain the intensities of Raman scattered light in a culture capable of producing virus particles are taken from samples extracted from the primary culturing environment in which the virus particles are produced following one or more liquid handling steps. In particular embodiments, the methods disclosed herein may comprise a step of sampling.

The origin of the sample used in the methods described herein may be the cell culture in which the virus is being produced. The sample therefore may be one of culture medium (e.g., DMEM, MEM, SFII, LVMAX, Texmacs, or PBS optionally including serum, L-glutamine and/or other components), which may additionally comprise packaging cells, e.g., if taken during a viral production process. Alternatively, the sample can be a partially purified or cell-free sample obtained during virus recovery. The sample may be a sample virus for medical use, e.g., which requires quality testing prior to marketing, sale or use. The sample could further be a sample from a subject (e.g., a human or mammalian subject) who is suspected of being infected by a virus. Accordingly, the sample may be a biological same, such as a blood, saliva, sputum, plasma, serum, cerebrospinal fluid, urine or fecal sample. Other sources of samples include from open water or public water supplies.

The methods of determining viral titer in a sample as described herein involve irradiating the sample with a light source and acquiring a Raman spectrum of the sample. Raman spectroscopy measures changes in the wavenumber of monochromatic light scattered by samples to provide information on their chemical composition, physical state and environment. This is possible because of the way in which the incident light photons interact with the vibrational modes that are present in the molecules that comprise the sample. These modes possess specific vibrational frequencies and scattering intensities under a set of given physical conditions and this makes it possible to quantify the amount of a given analyte of interest. Unlike infrared absorption spectroscopy where the absorption of light of different energies from a broadband light source is measured, in Raman spectroscopy the difference in energy of the monochromatic incident light to the scattered light is measured; this is known as the Raman shift.

The Raman spectra provides a "molecular fingerprint", enabling qualitative and quantitative analysis of samples, by providing information about the vibrational state of molecules. Many molecules have atomic bonds capable of existing in a number of vibrational states. Such molecules are able to absorb incident radiation that matches a transition between two of its allowed vibrational states and to subsequently emit the radiation. Most often, absorbed radiation is re-radiated at the same wavelength, a process designated Rayleigh or elastic scattering. In some instances, the re-radiated radiation can contain slightly more or slightly less energy than the absorbed radiation (depending on the allowable vibrational states and the initial and final vibrational states of the molecule). The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light which differs in frequency can be more easily distinguished from the Rayleigh scattered light.

In any embodiment, the Raman spectroscopy utilized in accordance with the methods disclosed herein is surface enhanced Raman spectroscopy (SERS). SERS is a surface-sensitive technique that enhances Raman scattering by molecules adsorbed on rough metal surfaces (e.g., roughened silver or gold surfaces) or by nanostructures such as plasmonic-magnetic silica nanotubes on a substrate.

In any embodiments, the application of SERS in the method of determining viral titer as described herein is carried out using a planar (or flat) substrate, such as a silicon, quartz, or glass substrate. Planar substrates may also be made of materials including, but not limited to, semiconductors (e.g., Si, GaAs, GaAsP, and Ge), oxides (e.g., $SiO_2$, $Al_2O_3$), and polymers (e.g., polystyrene, polyacetylene, polyethylene, etc.). In other embodiments the substrate is a non-planar substrate such as a cylindrical or conical substrate (e.g., an optical fiber or pipette tip). The substrate can be a microfabricated or nanofabricated substrate, such as a substrate with a regular array of micropatterns, such as a dot array, line array, or well array, or similar nanopatterns. In one embodiment, SERS in accordance with the methods described herein is performed using a metal substrate, where the metal selected from gold, silver, copper, and platinum, and alloys thereof. In one embodiment, the SERS for determining viral titer is performed on a gold substrate. In another embodiment, the SERS for determining viral titer is performed using a silver substrate.

In any embodiment, the application of SERS in the methods disclosed herein is carried out using a substrate modified to contain nanostructures. Suitable nanostructures include, but are not limited to, nanorods, nanowires, nanotubes, nanospirals, nanospheres, nanotriangles, nanostars, combinations thereof, and the like, and uniform arrays of each. The nanostructures (of the types described above) can be fabricated of one or more materials such as, but not limited to, a metal, a metal oxide, a metal nitride, a metal oxynitride, a metal carbide, a doped material, a polymer, a multicomponent compound, a compound (e.g., a compound or precursor compound, or an organic or inorganic compound), and combinations thereof. The metals can include, but are not limited to, silver, nickel, aluminum, silicon, gold, platinum, palladium, titanium, copper, cobalt, zinc, other transition metals, composites thereof, oxides thereof, nitrides thereof, silicides thereof, phosphides thereof, oxynitrides thereof, carbides thereof, and combinations thereof. In any embodiment, the materials are silver or gold. In any embodiment, the composition of the nanostructures is the same as that of the substrate material. In any embodiment, the composition of the nanostructure is different than the substrate material.

A number of commercially available SERS substrates can be used in carrying out the disclosed methods, including without limitation various SERS substrates available from Silmeco ApS (Copenhagen, Denmark), Horiba Scientific (Piscataway, NJ), Ocean Optics (Orlando, FL), Ato ID (Vilnius, Lithuania), Enhanced Spectrometry (San Jose, CA), and SERSitive (Warsaw, Poland). Alternatively, persons of skill in the art will, of course, understand that customized SERS substrates can alternatively be used, and these may be customized with respect to the nanostructuring materials, as well as any surface-bound reagents to promote virus particle binding/orientation.

The method of the present disclosure involves providing a sample in which information regarding the viral titer is required, and introducing the sample onto the substrate or nanostructures on the substrate, irradiating the sample with a light source, and acquiring a Raman spectrum of the sample that will be used to determine the viral titer in the sample. As noted above and in the examples, the sample to be evaluated in undiluted form, using one or more dilutions (including serial dilutions such as 10-fold, 100-fold, etc.), or both.

In any embodiment, the light source utilized for irradiating the sample is a narrow bandwidth laser. Suitable wavelengths include, without limitation, wavelengths between 300-1200 nm, 350-1100 nm, 400-1100 nm, 400-1064 nm, 450-1064 nm, 500-1064 nm, 550-1064 nm, 600-1064 nm, 650-1064 nm, 700-1064 nm, 450-1100 nm, or 500-1100 nm. In one embodiment, the light source is a narrow bandwidth laser with a wavelength between 550-1064 nm. In one embodiment, the light source is a narrow bandwidth laser with a wavelength between 400-1064 nm.

In any embodiment, the light source is a narrow bandwidth laser with a wavelength of about 800 nm, about 785 nm, about 750 nm, about 725 nm, about 700 nm, about 675 nm, about 650 nm, about 625 nm, about 600 nm, about 575 nm, about 550 nm, about 532 nm, about 525 nm, or about 500 nm. Preferably, the light source is a narrow bandwidth laser with a wavelength of about 785 nm, about 640 (e.g., 638 nm), or about 532 nm.

In any embodiment, the step of acquiring a Raman spectrum from a sample in accordance with the methods described herein includes acquiring a spectrum with an exposure time of about 100 ms, 150 ms, 200 ms, 250 ms, 300 ms, 350 ms, 400 ms, 450 ms, 500 ms, 550 ms, 600 ms, 650 ms, 700 ms, 750 ms, 800 ms, 850 ms, 900 ms, 950 ms, 1000 ms, or >1000 ms. In any embodiment, the Raman spectrum is acquired using an exposure time of about 250 ms.

Raman signal strength is directly proportional to the power of the Raman laser that is used to excite the sample. The more laser power that is utilized the larger the Raman signal will be and the particular laser power utilized can be optimized for a particular sample. However, in any embodiment, the spectrum of samples containing virus can be acquired using a Raman laser having a power of about 1.9 mW, about 1.8 mW, about 1.7 mW, about 1.6 mW, about 1.50 mW, about 1.4 mW, about 1.3 mW, about 1.2 mW, about 1.1 mW, about 1 mW, about 0.9 mW, about 0.8 mW, about 0.7 mW, 0.6 mW, or 0.5 about mW. In any embodiment, the spectra are acquired with a Raman laser having a power of about 1.50 mW. In any embodiment, the spectra are acquired with a Raman laser having a power of 0.6 mW.

The Raman spectra obtained from irradiating a sample with a light source is subsequently analyzed and a score for a virus component from the Raman spectrum is extracted. The peaks which are obtained for a particular Raman spectrum, at particular wavelengths, may correspond to viral particle specific amino acids (e.g., present in capsid proteins, etc.) or nucleic acids (e.g., RNA or DNA encapsulated by the viral particle), or may correspond to molecules/compounds which are non-viral (e.g. metabolites in the culture) but arise from the presence of the virus in the same. In this way, the Raman spectroscopy can be utilized to directly or indirectly detect the presence of virus in a sample, which can subsequently be scored and applied to a corresponding model utilized to determine the viral titer in the sample. For example, as described herein, suitable models for determining viral titer in accordance with the methods described herein include virus particle-specific calibration curves. Thus, the virus particle-specific component utilized to generate the model, is the virus component analyzed and scored from Raman spectrum obtained from an experimental sample (i.e., sample containing an unknown viral titer). Once a score for a virus particle specific component is extracted from the Raman spectrum, it is applied to the model to quantify a virus particle-specific titer.

Another aspect of the present disclosure is directed to a method for generating a model suitable for quantifying viral titer in a sample. This method comprises providing two or more samples, each sample containing a known virus type and corresponding titer and subjecting each sample to Raman spectroscopy to produce a reference spectrum for each known virus type and titer. The method further involves identifying a virus type-specific component from the reference spectra, and determining a score for said component for each sample of known virus type and known titer. The method further involves generating the model for quantifying viral titer based on the determined scores.

In order to create a model suitable for quantifying viral titer in a sample, several samples containing a known virus type and a known amount of the corresponding virus titer are analyzed using Raman spectroscopy, in particular SERS. For some models, two or more samples are analyzed using Raman spectroscopy. To create other models, three or more samples, four or more samples, five or more samples, six or more samples, seven or more samples, eight or more samples, nine or more samples, ten or more samples, fifteen or more, or twenty or more samples are required.

One or more Raman spectra for each sample containing a known virus type and a known amount of the corresponding virus titer are collected. In some embodiments, one or more spectra is/are collected for each of these samples. For example, two or more, three or more, four or more, five or more, ten or more, twenty of more, thirty or more, forty or more, fifty or more, sixty or more, seventy or more, eighty or more, ninety or more, 100 or more, 200 or more, 300 or more, 400 or more, or 500 or more spectra are collected for each of these samples.

In accordance with this aspect of the disclosure, the sample is subject to Raman spectroscopy as described supra. In any embodiment, the Raman spectroscopy is Surface Enhanced Raman spectroscopy as described supra, where the spectra are obtained from the sample on a metallic substrate (e.g., gold or silver) and/or nanostructure as described supra.

In any embodiment, the light source utilized for irradiating the sample to obtain the reference spectra is a narrow bandwidth laser. Suitable wavelengths include, without limitation, wavelengths between 300-1200 nm, 350-1100 nm, 400-1100 nm, 400-1064 nm, 450-1064 nm, 500-1064 nm, 550-1064 nm, 600-1064 nm, 650-1064 nm, 700-1064 nm, 450-1100 nm, or 500-1100 nm. In one embodiment, the light source is a narrow bandwidth laser with a wavelength between 550-1064 nm. In one embodiment, the light source is a narrow bandwidth laser with a wavelength between 400-1064 nm In any embodiments, the step of subjecting each sample to Raman spectroscopy to produce a reference spectrum for each known virus type and titer includes acquiring spectra with an exposure time of about 250 ms. In some embodiments, the spectra are acquired at about 1.9 mW, about 1.8 mW, about 1.7 mW, about 1.6 mW, about 1.5 mW, about 1.4 mW, about 1.3 mW, about 1.2 mW, about 1.1 mW, about 1 mW, about 0.9 mW, about 0.8 mW, about 0.7 mW, about 0.6 mW, about 0.5 mW, about 0.4 mW, about 0.3 mW, about 0.2 mW, or about 0.1 mW.

In any embodiment, the step of subjecting each sample to Raman spectroscopy to produce a reference spectrum for each known virus type and titer includes acquiring spectra with an exposure time of about 100 ms, 150 ms, 200 ms, 250 ms, 300 ms, 350 ms, 400 ms, 450 ms, 500 ms, 550 ms, 600 ms, 650 ms, 700 ms, 750 ms, 800 ms, 850 ms, 900 ms, 950 ms, 1000 ms, or >1000 ms. In any embodiment, the Raman spectra are acquired using an exposure time of about 250 ms.

In any embodiment, the step of subjecting each sample to Raman spectroscopy to produce a reference spectrum for each known virus type and titer includes acquiring spectra using a Raman laser having a power of about 1.9 mW, about 1.8 mW, about 1.7 mW, about 1.6 mW, about 1.50 mW, about 1.4 mW, about 1.3 mW, about 1.2 mW, about 1.1 mW, about 1 mW, about 0.9 mW, about 0.8 mW, about 0.7 mW, about 0.6 mW, about 0.5 mW, about 0.4 mW, about 0.3 mW, about 0.2 mW, or about 0.1 mW. In any embodiment, the spectra are acquired with a Raman laser having a power of about 1.50 mW or lower. In any embodiment, the spectra are acquired with a Raman laser having a power of 0.6 mW or lower.

The Raman spectra collected from the samples containing a known virus type and a known amount of the corresponding virus titer is then analyzed to identify a virus type-specific component from the reference spectra. In some embodiments, the reference spectrum for each sample is produced by analyzing two or more spectra of said sample. Alternatively, the reference spectrum for each sample is produced by analyzing three or more, four or more, five or more, ten or more, twenty of more, thirty or more, forty or more, fifty or more, sixty or more, seventy or more, eighty or more, ninety or more, 100 or more spectra, 200 or more, 300 or more, 400 or more, or 500 or more spectra of said sample.

In some embodiments, one or more background Raman spectra is collected. Such background spectra can be collected from a control sample, i.e., a sample corresponding to the viral sample in composition, but not containing virus. For example, suitable background spectra may be obtained from samples of water, culture medium, or other buffer solution that match the virus containing samples in composition but are virus-free. In some embodiments, the two or more spectra from the background are averaged to create the background Raman spectrum. In some embodiments, the background spectrum is subtracted from each of the reference spectrum before the spectrum from the virus containing sample is analyzed.

In some embodiments, the spectra collected from the samples is truncated before it is analyzed. Preferably, the spectra are truncated, for example, to a spectral range of 300 $cm^{-1}$ to 2000 $cm^{-1}$, 300 $cm^{-1}$ to 1900 $cm^{-1}$, 300 $cm^{-1}$ to 1800 $cm^{-1}$, 300 $cm^{-1}$ to 1700 $cm^{-1}$, 300 $cm^{-1}$ to 1600 $cm^{-1}$, 300 $cm^{-1}$ to 1500 $cm^{-1}$, 350 $cm^{-1}$ to 1700 $cm^{-1}$, 350 $cm^{-1}$ to 1600 $cm^{-1}$, 400 $cm^{-1}$ to 1700 $cm^{-1}$, 400 $cm^{-1}$ to 1600 $cm^{-1}$, 450 $cm^{-1}$ to 1700 $cm^{-1}$, 450 $cm^{-1}$ to 1600 $cm^{-1}$, 500 $cm^{-1}$ to 1700 $cm^{-1}$, 500 $cm^{-1}$ to 1600 $cm^{-1}$, 550 $cm^{-1}$ to 1700 $cm^{-1}$, 550 $cm^{-1}$ to 1600 $cm^{-1}$, 600 $cm^{-1}$ to 1700 $cm^{-1}$, or 600 $cm^{-1}$ to 1600 $cm^{-1}$. More preferably, the spectra are truncated to a spectral range of 500 $cm^{-1}$ to 1600 $cm^{-1}$.

In order to identify a virus type-specific component from the reference spectra (i.e., spectra from samples of known virus type and known titer) a chemometric analysis is used to analyze (decompose) the two or more reference spectra produced from each of the two or more samples. Using this chemometric analysis, one or more components of variation between the reference spectra are identified and the scores for each component are assessed. Suitable chemometric analyses that can be utilized to analyze the reference spectra produced from the samples are known in the art and include, without limitation, multivariate curve resolution, principal component analysis, discriminant analysis (e.g., linear discriminant analysis, partial least squares discriminant analysis), K means clustering analysis, neural networks analysis, regression analysis (e.g., principal component regression analysis, partial least squares regression analysis), and class-modeling methods (e.g., soft independent modeling of class analogies) (see e.g., Biancolillo and Marini, "Chemometric Methods for Spectroscopy-Based Pharmaceutical Analysis," *Front. Chem.* 6:576 (2018), which is hereby incorporated by reference in its entirety). Based on these analyses one or more spectral components correlating with a particular virus type (i.e., a virus-type specific component) is identified and scored.

The scores of the virus type-specific component for each sample containing a known virus type and a known amount of the corresponding virus titer are used to prepare a model suitable for quantifying viral titer of an unknown virus titer in test or experimental sample. In any embodiment, the model generated is a virus type-specific calibration curve or standard curve. Thus, the criteria for selecting one virus particle specific component over another virus particle specific component will depend on the ability of the component to discriminate against virus particles or empty capsids that are not of interest from those that are of interest, as well as the medium in which the virus particles reside. It is also important to examine the components for features that are characteristic of (i.e., specificity to) the virus particles, empty capsids, or genetic material of interest, ensuring that the spectrum obtained looks like reference spectra of the virus particles or empty capsids of interest, or has expected features.

The reference spectra utilized to develop the model suitable for quantifying viral titer in a sample is preferably generated from two or more samples comprising known virus types of interest. In some embodiments, the two or more samples comprise two or more different virus types, e.g., virus types differing by one or more genetic elements (e.g., genetic insertions, deletions, substitutions or translocations). For example, if the model suitable for quantifying viral titer in a sample is suitable for identifying a lentivirus comprising an exogenous gene insertion, then reference spectra utilized to develop the model are collected from samples comprising known amounts of the modified lentivirus of interest, and optionally, samples comprising known amounts of wild type lentivirus. This allows for identification of a spectral component that is specific to the modified lentivirus as compared to wild type lentivirus, and the generation of a calibration curve specific for determining titers of the modified lentivirus in a sample.

As described supra, the method of generating a model suitable for quantifying viral titer in a sample is carried out utilizing sample comprising known types and amounts of any virus type. For example, suitable samples comprise, without limitation, samples containing retrovirus particles, retrovirus-like particles, adenovirus particles, adenovirus-like particles, adeno-associated virus particles, adeno-associated virus-like particles, herpes simplex virus particles, and herpes simplex virus-like particles. In some embodiments, the virus is a retrovirus particle, such as a lentivirus particle.

EXAMPLES

The examples below are intended to exemplify the practice of embodiments of the disclosure but are by no means intended to limit the scope thereof.

Materials and Methods for Examples 1 and 2

Materials and Reagents: Gold and silver SERS substrates were purchased from Silmeco (SERStrate). Ultrapure water (18.2 MΩ cm) was acquired from a Milli-Q system. Fused silica capillary with 75.9 μm i.d. and 150.0 μm o.d. was purchased from Polymicro Technologies. Hydrochloric acid, LV-MAX production medium, fetal bovine serum (FBS), phosphate buffered saline (PBS), Eagle's minimum essential medium (EMEM), and LentiArray CRISPR Negative Control Lentivirus, human non-targeting with green fluorescent protein (GFP) and without GFP were purchased from ThermoFisher Scientific. Human HT-1080 fibrosarcoma cells (ATCC CCL-121) were obtained from American Type Culture Collection (ATCC). Polybrene and isopropanol were purchased from Sigma Aldrich. Orange Tough resin was purchased from Prusa Research.

Sample Preparation: All virus solutions were prepared in LV-MAX production medium. For SERS calibration, solutions were prepared of LentiArray CRISPR Negative Control Lentivirus, human non-targeting with GFP and without GFP each with concentrations ranging from 500 TU/mL to 50,000 TU/mL.

3D Printing: A 3D printed SERS substrate holder was produced using an Original Prusa SL1 for use with gold substrates. For silver substrates a 3D printed flow cell was developed and used. CAD designs were created in Autodesk Fusion 360 and then sliced using PrusaSlicer software. Orange Tough resin was used for all printed objects. The objects were then washed for 10 minutes in isopropanol, dried for 2 minutes, and cured for 2 minutes in an Original Prusa CW1 Curing and Washing Machine. The objects were then rinsed with Milli-Q water.

SERS Flow Cell Preparation: Silver and gold substrates were heated at 175° C. on a hotplate for 10 minutes. A gold Silmeco substrate was placed into the 3D printed SERS substrate holder with a fused silica capillary affixed on top. This substrate holder was then placed into a previously described sheath flow SERS cell in place of the glass slide (Negri et al., "Ultrasensitive Surface-Enhanced Raman Scattering Flow Detector Using Hydrodynamic Focusing," *Analytical Chemistry* 85(21):10159-10166 (2003), which is hereby incorporated by reference in its entirety). A silver Silmeco substrate was placed into the 3D printed flow cell, which was then glued together using clear Gorilla glue. Prior to Raman detection, 0.1 M HCl was flowed over the silver substrates to wash away any contaminants that remained on the surface. Water was run through the flow cells to rinse both silver and gold surfaces before Raman measurements.

Raman Measurements: Raman spectroscopy was performed using a home-built instrument. A 785 nm or 532 nm laser (Oxxius) was focused onto the SERS substrate using a 40×water immersion objective (NA=0.8). Raman scattering was collected through the same objective and directed to an Isoplane SCT-320 spectrograph equipped with a ProEM: $1600^2$ eXcelon 3 CCD detector (Princeton Instruments). Spectra were acquired with an exposure time of 250 ms and 1.50 mW (785 nm) or 0.60 mW (532 nm) of laser power at the sample. 240 spectra were acquired in series per acquisition. The virus samples were injected through the fused silica capillary with a water sheath fluid for experiments using gold substrates. Prior to and during SERS spectral acquisition the sheath and sample flows were stopped. After spectral acquisition, the sheath flow was resumed, and the sample flow was switched to water to clean the surface before injecting the next sample.

Data Analysis: All spectra were processed using Matlab R2018b (Mathworks). Multivariate curve resolution (MCR) was performed using the PLS Toolbox (Eigenvector Research Inc.) in Matlab. Prior to MCR analysis, a background spectrum of water on the SERS substrate was subtracted from each lentivirus spectrum and the spectra were then truncated to a spectral range of 500 cm$^{-1}$ to 1600 cm$^{-1}$. The average score on component 2 was plotted against concentration to develop a calibration curve.

Lentiviral Transduction: HT-1080 cells were cultured in EMEM supplemented with 10% FBS. 10,000 cells were seeded in 100 µL culture medium per well in a 96-well plate and incubated overnight in a humidified atmosphere of 5% $CO_2$ and a temperature of 37° C. LentiArray™ CRISPR Negative Control Lentivirus, human, non-targeting, with GFP were thawed on ice for an hour before transduction. Transduction media was prepared by adding polybrene to EMEM supplemented with FBS to a final concentration of 8 µg/mL. A 4-log serial dilution was prepared in triplicate by sequentially diluting the virus solution into transduction media. The media was removed from the cells and 100 µL of each dilution was added into a well. The plate was swirled for 5 minutes to distribute the virus. The cells were then incubated for 24 hours. Next, the lentivirus transduction media was replaced with EMEM supplemented with 10% FBS and then the cells were incubated for another 24 hours. Then, the media was removed from the cells and replaced with PBS before imaging.

Fluorescence Imaging: The cells were imaged with an upright Olympus microscope using a GFP filter cube and blue LED (Thorlabs) for excitation. Data analysis of brightfield and fluorescence images was performed using ImageJ, and a cell counter plugin was used to count cells. Lentiviral titer was then calculated using Equation 1 below.

$$\text{Titer}\left(\frac{TU}{mL}\right) = \text{fraction of fluorescent cells} \times \frac{\text{Cells per well}}{\text{volume of media per well}} \times \text{dilution of stock} \quad \text{(Eq. 1)}$$

Example 1: Detecting and Distinguishing Between Lentivirus Particles Using a Gold SERS Substrate The experimental design is shown on FIG. 1. The SERS spectra from the lentivirus particles either with an encoding a GFP gene or without were acquired in the LV-MAX virus production media. Each virus type was injected in media onto the SERS substrate and measured without flow. By measuring in media, minimal sample pretreatment is necessary. Additionally, the aqueous environment improves heat dissipation from the excited nanostructures, which has been shown to enable improved signal generation without thermal damage to sample or substrate (Zeng et al., "Photothermal Microscopy of Coupled Nanostructures and the Impact of Nanoscale Heating in Surface Enhanced Raman Spectroscopy," *J. Phys. Chem. C* 121(21):11623-11631 (2017), which is hereby incorporated by reference in its entirety).

The resulting spectra from SERS measurements of particles were used to generate a multivariate curve resolution (MCR) model representative of the number of particles containing the GFP gene. Prior to SERS acquisition the flow cell was rinsed with water to clean the surface and capillary, then the virus sample was injected through the capillary and both sheath and sample flows were stopped. Following SERS acquisition, the substrate's surface was cleaned using water. Spectra of water on the substrate were acquired prior to analyzing each concentration, and then subtracted out of the SERS spectra prior to analysis to account for the background signal of the substrate.

Figure 2A:
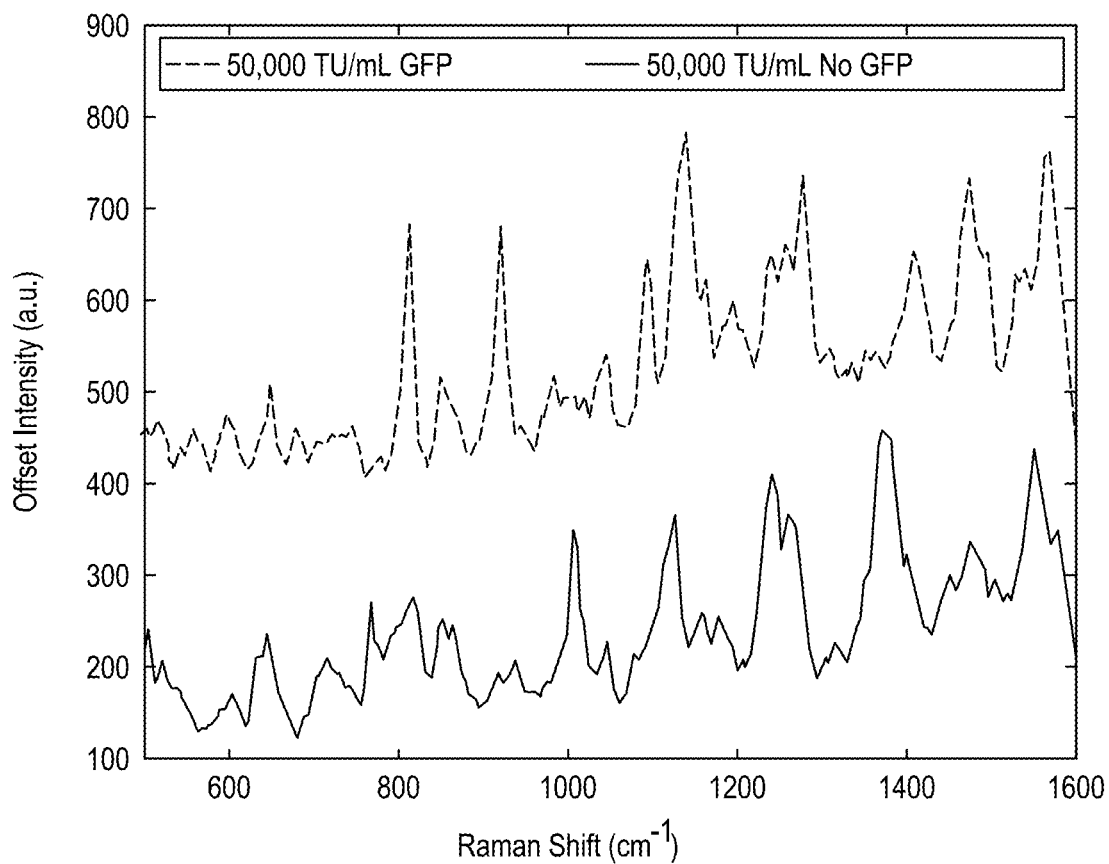
FIGS. 2A-2B show SERS spectra acquired for LentiArray CRISPR negative control lentivirus with GFP (grey) and without GFP (black) at 50,000 TU/mL on a gold substrate (FIG. 2A) and different concentrations of LentiArray CRISPR negative control lentivirus with GFP (FIG. 2B). The shaded region shows the standard deviation across all spectra obtained at each concentration.
Figure 2B:
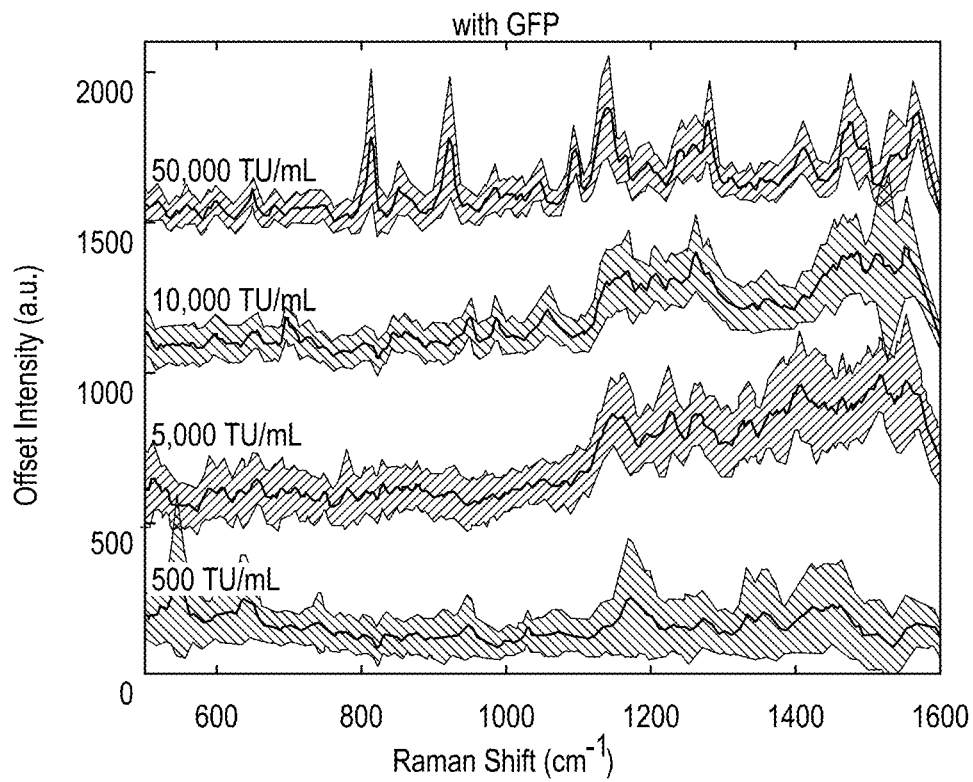

SERS spectra of virus particles acquired by injecting the lentivirus samples into a sheath flow SERS cell with a gold substrate are shown in FIGS. 2A-2B. FIG. 2A compares the average SERS spectrum acquired from the virus with and without the GFP gene at the highest concentration analyzed. The spectra for each type of virus particle show Raman bands associated with amino acids and nucleic acids. Common peaks shared between the two types of particles include the bands at 813 cm$^{-1}$ associated with the phosphate backbone stretch in RNA (Shanmukh et al., "Rapid and Sensitive Detection of Respiratory Virus Molecular Signatures Using a Silver Nanorod Array SERS Substrate," *Nano Letters* 6(11):2630-2636 (2006), which is hereby incorporated by reference in its entirety), 851 cm$^{-1}$ assigned to tyrosine (Shanmukh et al., "Rapid and Sensitive Detection of Respiratory Virus Molecular Signatures Using a Silver Nanorod Array SERS Substrate," *Nano Letters* 6(11):2630-2636 (2006), which is hereby incorporated by reference in its entirety), 1007 cm$^{-1}$ assigned to phenylalanine (Ashton et al., "pH-Induced Conformational Transitions in α-Lactalbumin Investigated with Two-Dimensional Raman Correlation Variance Plots and Moving Windows," *Journal of Molecular Structure* 974(1-3):132-138 (2010), which is hereby incorporated by reference in its entirety), 1046 cm$^{-1}$ assigned to cytosine (Shanmukh et al., "Rapid and Sensitive Detection of Respiratory Virus Molecular Signatures Using a Silver Nanorod Array SERS Substrate," *Nano Letters* 6(11):2630-2636 (2006); Negri et al., "Detection of Genetic Markers Related to High Pathogenicity in Influenza by SERS," *The Analyst* 138(17):4877-4884 (2013), which are hereby incorporated by reference in their entirety), 1242 cm$^{-1}$ which arises from the amide III stretch (Ashton et al., "pH-Induced Conformational Transitions in α-Lactalbumin Investigated with Two-Dimensional Raman Correlation Variance Plots and Moving Windows," *Journal of Molecular Structure* 974(1-3):132-138 (2010), which is hereby incorporated by reference in its entirety), and 1475 cm$^{-1}$ associated with the CH2 scissoring of glutamate and aspartate (Negri et al., "Online SERS Detection of the 20 Proteinogenic 1-Amino Acids Separated by Capillary Zone Electrophoresis," *The Analyst* 139(22):5989-5998 (2014), which is hereby incorporated by reference in its entirety). Despite the similar structures of the two different virus particles, FIG. 2A also shows that there are differences in the SERS signals. Notable differences in the spectra include strong peaks at 812 and 921 cm$^{-1}$ arising from the phosphate backbone (Shanmukh et al., "Rapid and Sensitive Detection of Respiratory Virus Molecular Signatures Using a Silver Nanorod Array SERS Substrate," *Nano Letters* 6(11):2630-2636 (2006), which is hereby incorporated by reference in its entirety) and adenine (Suh et al., "Surface-Enhanced Raman Spectroscopy of Amino Acids and Nucleotide Bases Adsorbed on Silver," *J. Am. Chem. Soc.* 108(16):4711-4718 (1986), which is hereby incorporated by reference in its entirety) for the particles with GFP. These additional bands could arise due to the additional RNA in these particles compared to those without GFP. Also, a strong band at 1141 cm$^{-1}$ with a shoulder at 1164 cm$^{-1}$ are observed in the spectrum of the particles with GFP arising from phenylalanine and tryptophan, respectively (Negri et al., "Online SERS Detection of the 20 Proteinogenic 1-Amino Acids Separated by Capillary Zone Electrophoresis," *The Analyst* 139(22):5989-5998 (2014), which is hereby incorporated by reference in its entirety). Additionally, bands at 1280, 1410, and 1567 cm$^{-1}$ arising from arginine, histidine, and phenylalanine/tyrosine, respectively, are seen strongly in the spectra of particles containing GFP (Negri et al., "Online SERS Detection of the 20 Proteinogenic 1-Amino Acids Separated by Capillary Zone Electrophoresis," *The Analyst* 139(22): 5989-5998 (2014), which is hereby incorporated by reference in its entirety). These differences show that SERS is capable of detecting modifications of the genetic material within a virus particle at a concentration of 50,000 TU/mL.

Figure 3:
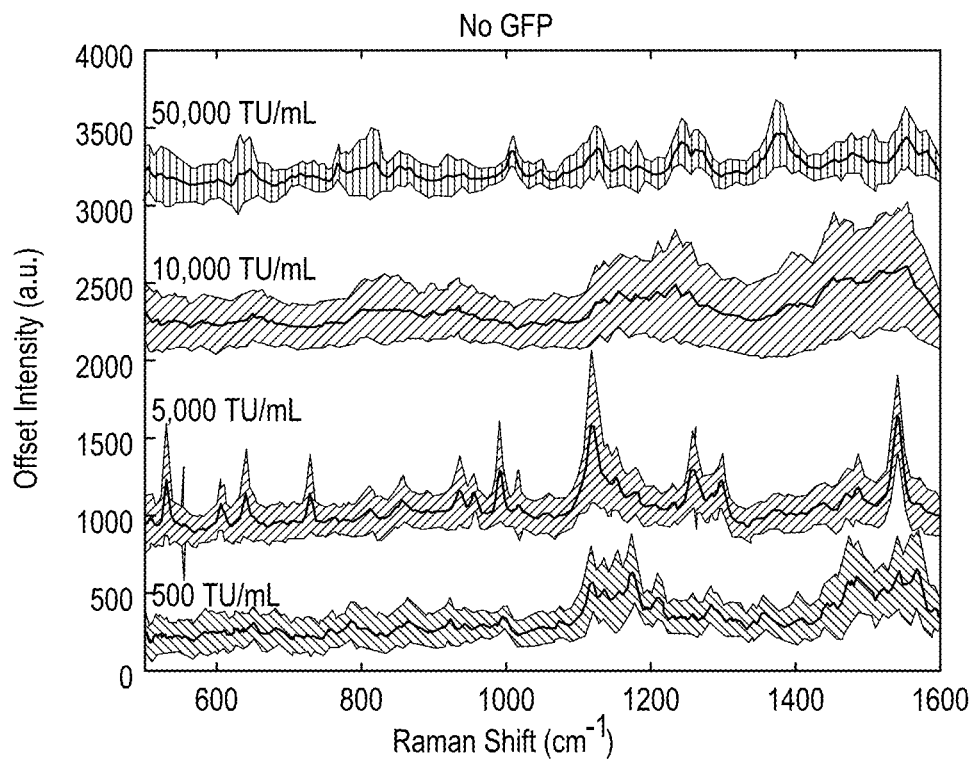
FIG. 3 is a graph showing SERS spectra of LentiArray CRISPR negative control lentivirus without GFP at various concentrations. The shaded region shows the standard deviation across all spectra acquired on gold substrates.

The spectra of the virus particles with GFP at various concentrations with the standard deviation shaded around it is shown in FIG. 2B. Due to the complexity of the virus particles' structure, there is variation in the average signals obtained for the same particle types. The peaks at 1164 and 1259 $cm^{-1}$, arising from tryptophan (Negri et al., "Online SERS Detection of the 20 Proteinogenic 1-Amino Acids Separated by Capillary Zone Electrophoresis," *The Analyst* 139(22):5989-5998 (2014), which is hereby incorporated by reference in its entirety) and the amide III stretch (Ashton et al., "pH-Induced Conformational Transitions in α-Lactalbumin Investigated with Two-Dimensional Raman Correlation Variance Plots and Moving Windows," *Journal of Molecular Structure* 974(1-3):132-138 (2010), which is hereby incorporated by reference in its entirety), were detected in all four concentrations. The peaks at 813 $cm^{-1}$ (phosphate backbone) (Shanmukh et al., "Rapid and Sensitive Detection of Respiratory Virus Molecular Signatures Using a Silver Nanorod Array SERS Substrate," *Nano Letters* 6(11):2630-2636 (2006), which is hereby incorporated by reference in its entirety), 923 $cm^{-1}$ (adenine) (Suh et al., "Surface-Enhanced Raman Spectroscopy of Amino Acids and Nucleotide Bases Adsorbed on Silver," *J. Am. Chem. Soc.* 108(16):4711-4718 (1986), which is hereby incorporated by reference in its entirety), 1095 $cm^{-1}$ (phosphate backbone) (Negri et al., "Detection of Genetic Markers Related to High Pathogenicity in Influenza by SERS," *The Analyst* 138(17): 4877-4884 (2013), which is hereby incorporated by reference in its entirety), 1475 $cm^{-1}$ (glutamate/aspartate) (Negri et al., "Online SERS Detection of the 20 Proteinogenic 1-Amino Acids Separated by Capillary Zone Electrophoresis," *The Analyst* 139(22):5989-5998 (2014), which is hereby incorporated by reference in its entirety), and 1575 $cm^{-1}$ (tryptophan) (Shanmukh et al., "Rapid and Sensitive Detection of Respiratory Virus Molecular Signatures Using a Silver Nanorod Array SERS Substrate," *Nano Letters* 6(11):2630-2636 (2006), which is hereby incorporated by reference in its entirety) showed the greatest increase in intensity in the highest concentration. The peaks consistently shown in the averages likely arise from the proteins found on the surface or capsid of the virus particle. Whereas, most of the peaks that show an increase in intensity arise from nucleic acids and the phosphate backbone of the genetic material within the capsid. The virus particles contain proteins and lipids on their surface surrounding a capsid containing genetic material. As expected, more modes arising from molecules on the surface of the virus than from the molecules within the capsid were observed. This is due to the surface of the virus directly interacting with the SERS substrate. However, it is expected that aromatic nucleic acids are close enough to the substrate to be detected by SERS. The difference in average signals for the different concentrations of virus particles could arise from different orientations of the particles on the SERS active surface, or different molecular components of the virus being in a hotspot, leading to different enhancements of the vibrational modes seen. The virus particles analyzed were spherical to oblong and 80-100 nm in diameter, much larger in size than the approximately 1 $nm^3$ volume associated with the hotspot on a SERS substrate, thus only a portion of the virus particle will be in a given hotspot. The average spectra for each concentration show differences in the bands observed, complicating the use of univariate analysis to determine the concentration dependence. The average SERS spectra for each concentration of the lentivirus particles without GFP is shown in FIG. 3 and show a similar trend.

Figure 4:
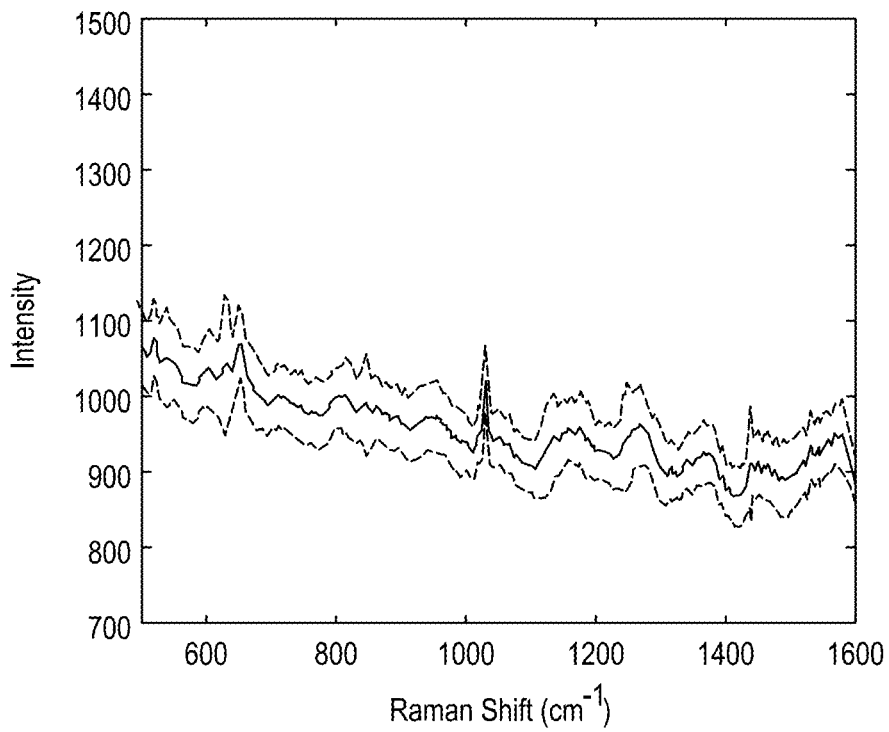
FIG. 4 is a graph showing average SERS spectrum of LV-MAX media acquired on a gold substrate with standard deviations outlined.

The lentivirus particles were diluted and stored in LV-MAX production medium. Pure LV-MAX medium was injected into the flow cell, and the spectra acquired is shown in FIG. 4. The media shows peaks at 653 $cm^{-1}$ and 1030 $cm^{-1}$, thus the signal obtained for the lentivirus particles arises from the virus particles themselves and not the media.

Figure 5A:
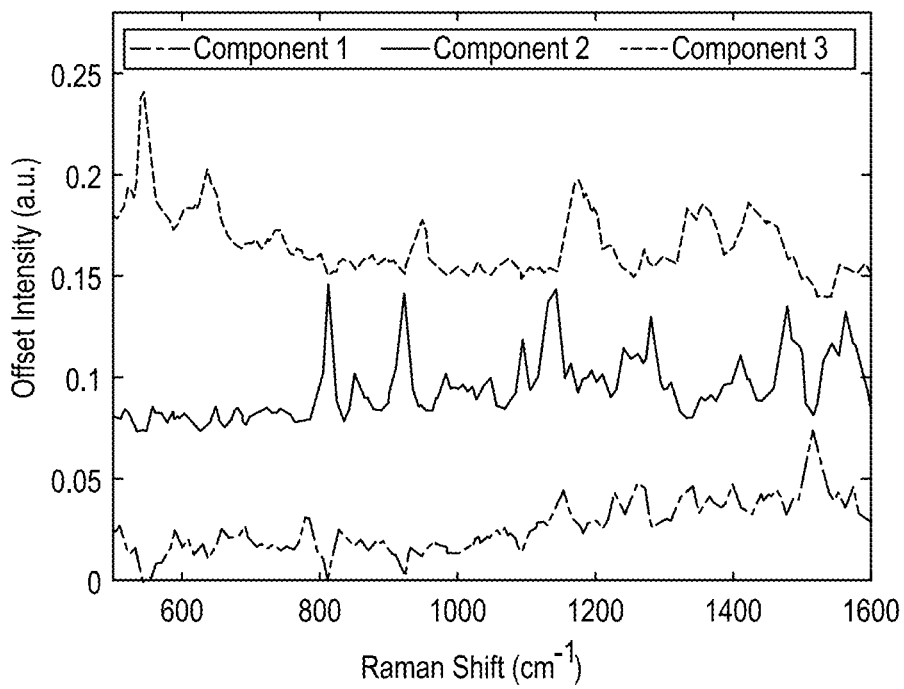
FIGS. 5A-5D show the MCR model for LentiArray CRISPR negative control lentivirus with GFP developed using spectra acquired at 500 TU/ml, 5,000 TU/mL, and 50,000 TU/mL. The model was validated using spectra of 10,000 TU/mL. Spectra of water were subtracted from each concentration prior to MCR analysis.
Figure 5B:
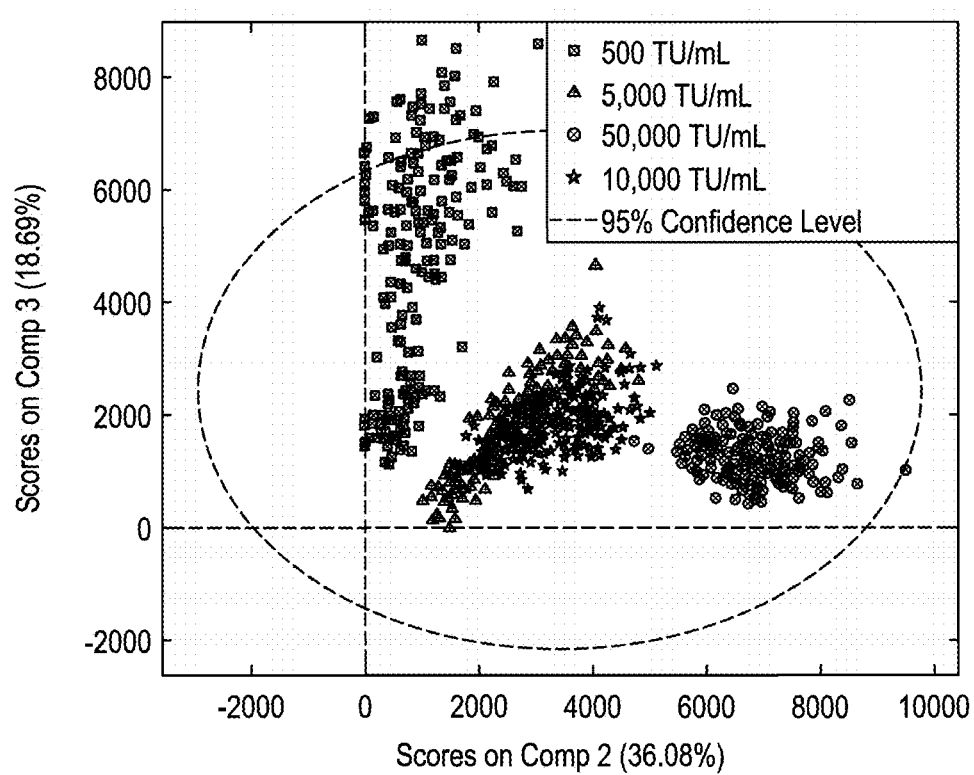
Figure 5C:
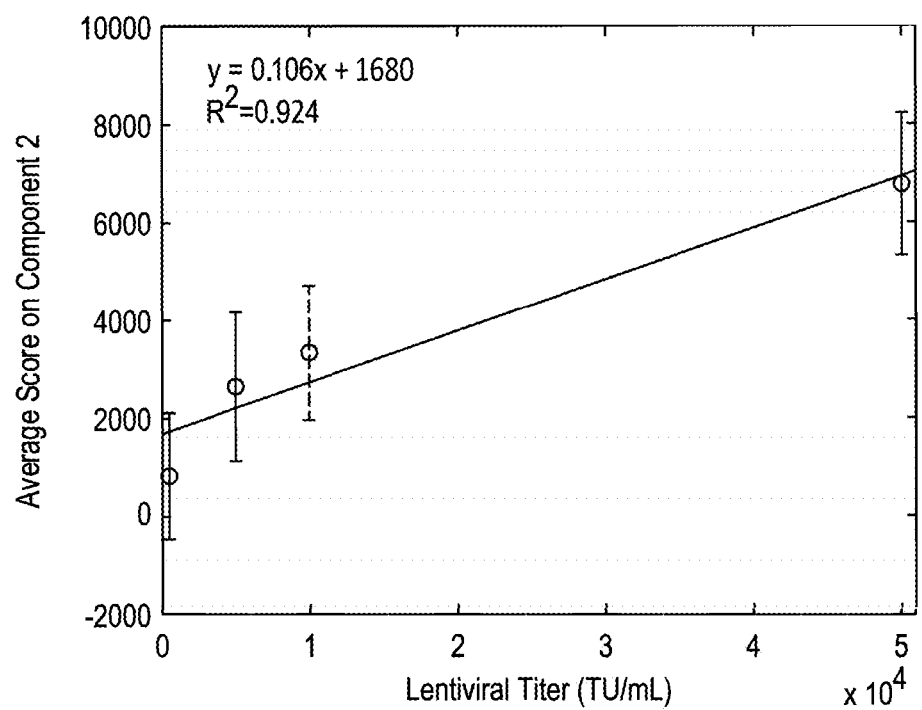

To determine viral titer, multivariate curve resolution (MCR) was performed to extract a component that correlates with the GFP vector. FIGS. 5A-5D show the three component model developed using spectra acquired from the lentivirus particles with GFP at concentrations of 500 TU/mL, 5,000 TU/mL, and 50,000 TU/mL. This model captured 95.47% of the variance in the data. The 10,000 TU/mL GFP particle spectra were used to validate this model. The model shows a linear relationship between the score on component 2 and the concentration of lentivirus with GFP (FIG. 5B). The average score on component 2 for each concentration was then plotted against viral titer to create a calibration for determining viral titer (FIG. 5C). The error bars on this curve represent the standard deviations of the measurements.

Figure 5D:
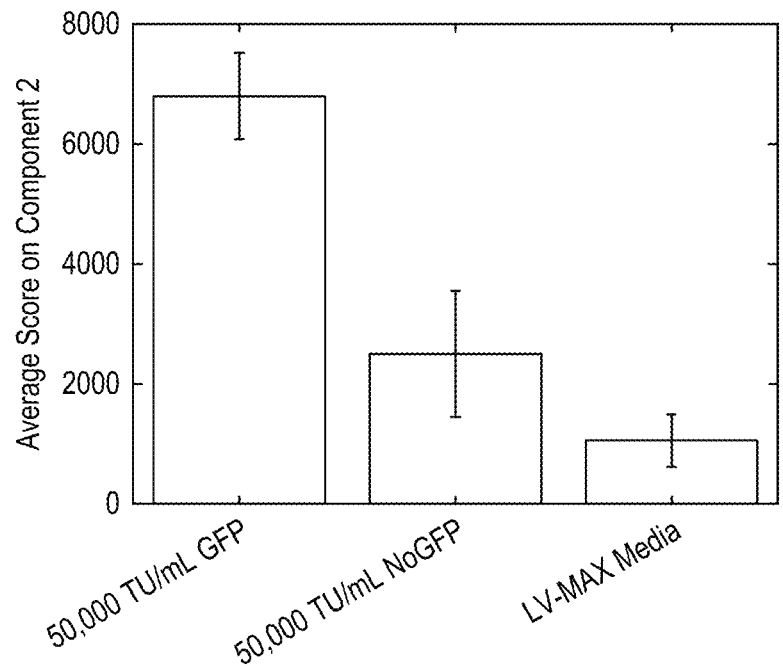
Figure 6:
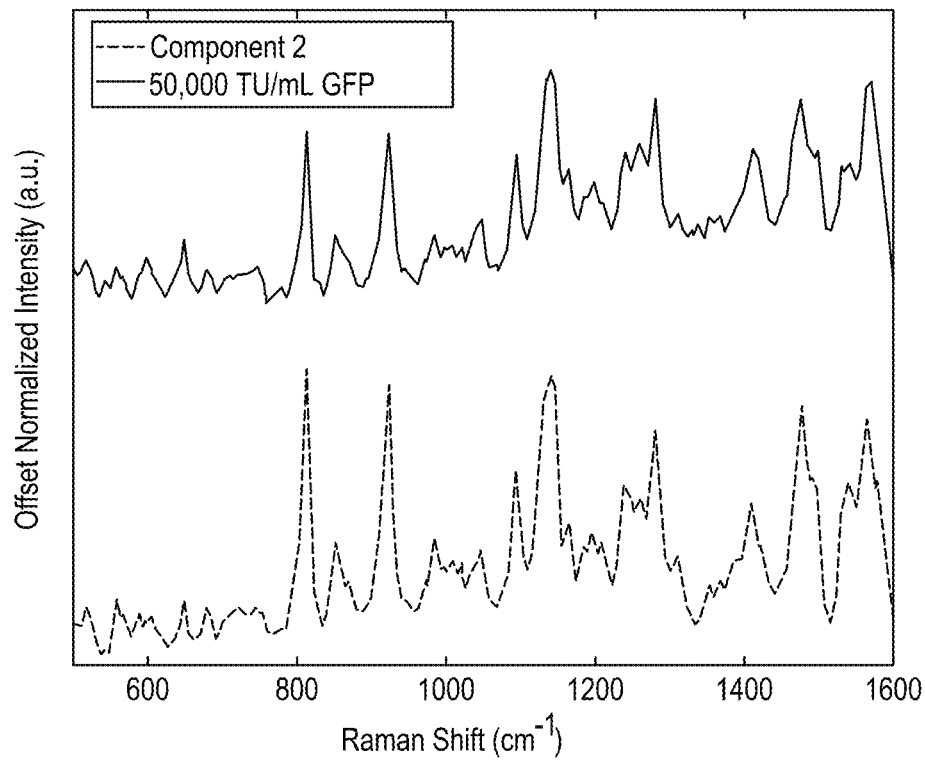
FIG. 6 is a graph showing average SERS spectra of highest concentration of lentivirus particles with GFP (black) and the component spectrum of the MCR model used to quantify the particles with GFP (grey).

The loading for component 2 shows a similar spectrum to that of the lentivirus particles containing the GFP vector at the highest concentration analyzed (FIG. 6). The peak assignments for the SERS bands observed in component 2 are shown in Table 1. To further confirm that this component spectrum arises from the particles with GFP, spectra of the particles without GFP at a concentration of 50,000 TU/mL were tested with the model. These spectra score lower on component 2 than those of the particles with GFP at the same concentration and the difference is statistically significant. This further suggests that this component is associated with the GFP vector. Spectra of LV-MAX media, shown in FIG. 4, were also tested with the model, and the scores for these spectra on component 2 are much lower than both types of lentivirus particles. The bar graph shown in FIG. 5D compares the scores for each of these samples and indicates that SERS is capable of distinguishing between the virus particles with and without the inserted gene. The scores of the particles without GFP have an average of 2500 on component 2, which is comparable to the scores for the particles with GFP at concentrations of 5,000 and 10,000 TU/mL. This is due to the high levels of scattering from the particles without the GFP gene which can interfere with quantification. However, commonly used viral titers are $10^5$ TU/mL or higher, which are greater than the titers shown in this study (Pivert et al., "A First Experience of Transduction for Differentiated HepaRG Cells using Lentiviral Technology," *Scientific Reports* 9(1):12910 (2019); Lim et al., "Identification of Newly Emerging Influenza Viruses by Surface-Enhanced Raman Spectroscopy," *Analytical Chemistry* 87(23):11652-11659 (2015); Bagnall et al., "Quantitative Dynamic Imaging of Immune Cell Signalling Using Lentiviral Gene Transfer," *Integrative Biology* 7(6):713-725 (2015); Guerreiro et al., "Detection and Quantification of Label-Free Infectious Adenovirus Using a Switch-On Cell-Based Fluorescent Biosensor," *ACS Sensors* 4(6):1654-1661 (2019), which are hereby incorporated by reference in their entirety).

TABLE 1

Peak Assignments for Component 2 Loading
Spectrum of the MCR Model Developed Using
SERS Spectra Acquired on Gold Substrates

| SERS Band (cm$^{-1}$) | Peak Assignments |
| --- | --- |
| 649 | Guanine |
| 681 | Adenine |
| 812 | Phosphate Backbone |
| 851 | Tyrosine |
| 921 | Adenine |
| 985 | Alanine |
| 1006 | Phenylalanine |
| 1046 | Cytosine |
| 1095 | Phosphate backbone |
| 1141 | Phenylalanine |
| 1195 | Cytosine |
| 1241 | Amide III |
| 1259 | Amide III |
| 1280 | Arginine |
| 1338 | Adenine |
| 1354 | Tryptophan |
| 1410 | Histidine |
| 1476 | Glutamate/Aspartate |
| 1540 | Adenine |
| 1567 | Phenylalanine/Tyrosine |

Figure 7:
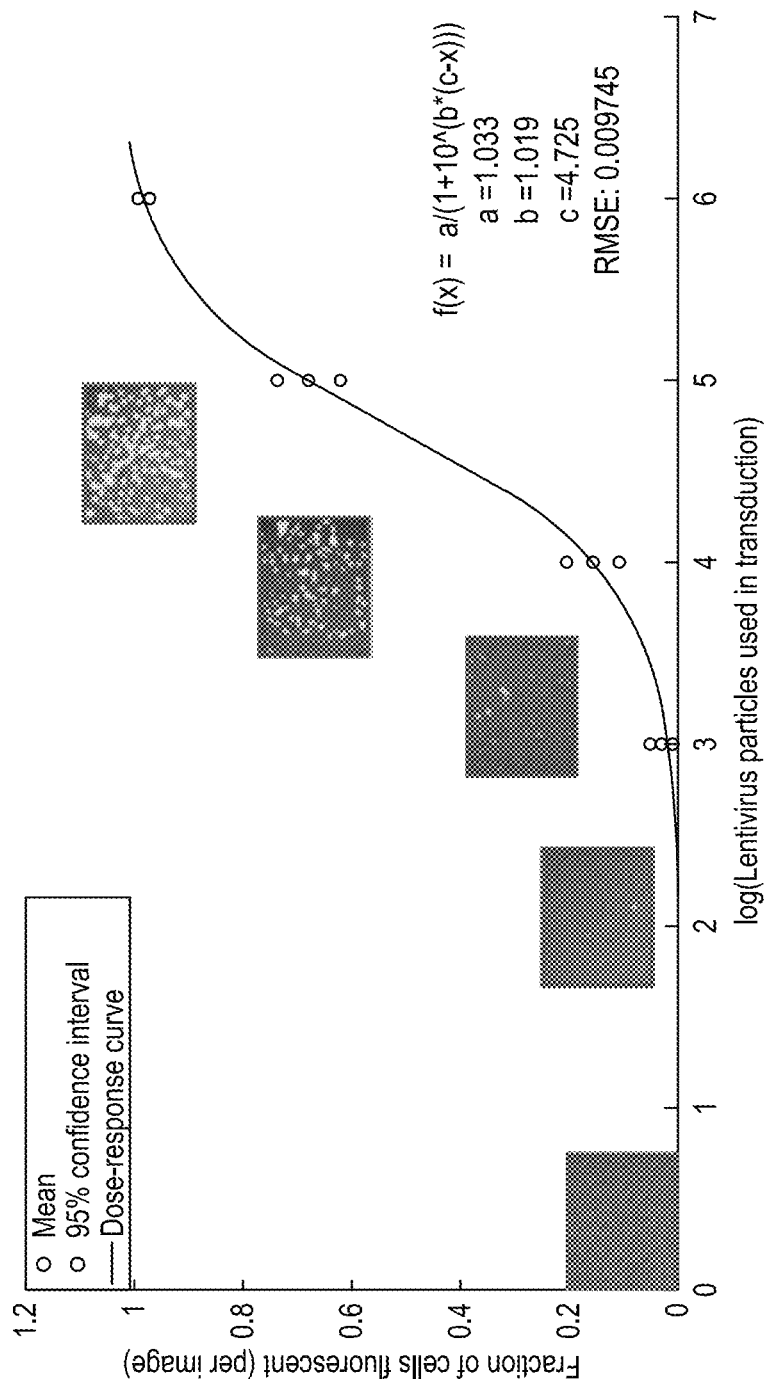
FIG. 7 is a graph showing determination of viral titer by cell fluorescence. Inset figures show fluorescence images overlaid on the bright field images at each concentration analyzed.

Fluorescence imaging was used to validate the viral titer determined by SERS. HT-1080 fibrosarcoma cells were transduced with the lentivirus encoding for GFP. A dose-response curve (FIG. 7) was created using the fraction of cells that were fluorescent and the log of the amount of lentivirus particles used for transduction. These results confirm the viral titer used for SERS experiments. Also, these images show that the lentivirus used is highly infectious at concentrations greater than $10^4$ TU/mL, which are similar to the concentrations SERS was used to distinguish between the two particle types.

Figure 8A:
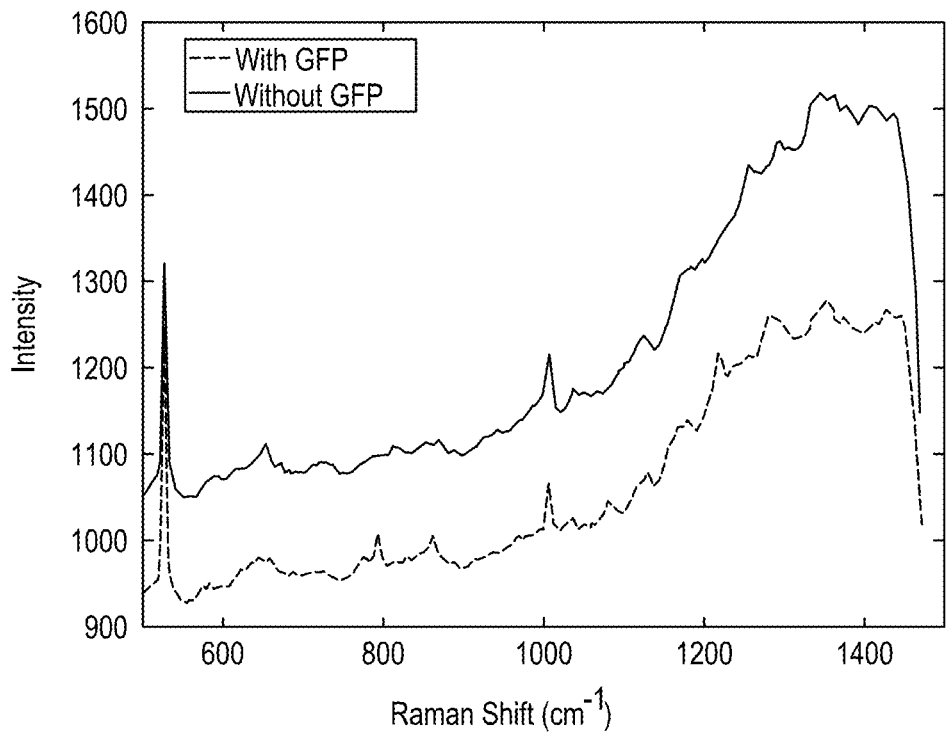
FIGS. 8A-8D show analysis of LentiArray CRISPR negative control lentivirus with and without GFP using silver SERS substrates and 532 nm laser excitation.
Figure 8B:
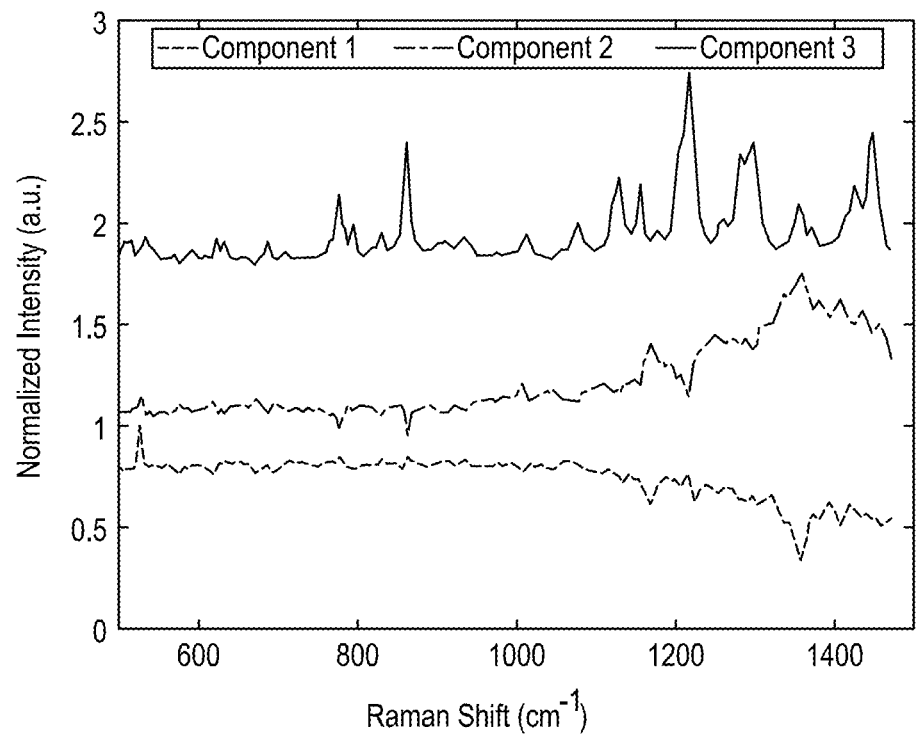
Figure 8C:
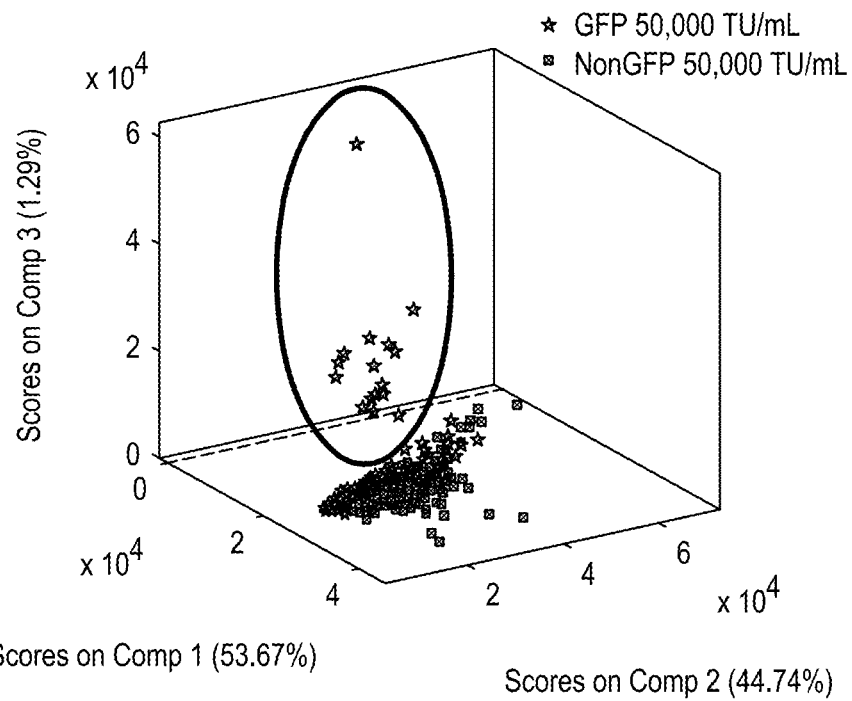

Example 2: Detecting and Distinguishing Between Lentivirus Particles Using a Silver SERS Substrate The SERS method of detecting and distinguishing between lentivirus particles was also performed using a silver SERS substrate and 532 nm excitation. Using the same lentiviruses studied previously, reference spectra were collected for each type of particle at a concentration of 50,000 TU/mL. The raw spectra collected of the lentivirus particles with and without the GFP gene are shown in FIG. 8A. A three component MCR model was built using all spectra collected for each particle, 740 spectra total for each type. The loading spectra for this model is shown in FIG. 8B, and the scores for each component are shown in FIG. 8C. In this model, components 1, 2, and 3 accounted for 53.67%, 44.74%, and 1.29% of the total variance in the data, respectively. The only spectra that score highly on component 3 are spectra from the lentivirus particles with GFP. Since these spectra could be separated from those of the lentivirus particles without GFP, this component can be associated with the GFP vector. Most of the spectra have similar scores on components 1 and 2, thus showing that the detection of the inserted gene can become complicated by the background signal from the lentiviruses themselves. The large and complex molecular structure of virus particles can scatter a lot of light and produce complex SERS signals. These signals can thus complicate the spectra that show the inserted gene and make detection and quantification of this gene more difficult. Although most of the spectra for both lentiviruses have similar scores on components 1 and 2, component 3 can be utilized to detect the inserted gene.

Figure 8D:
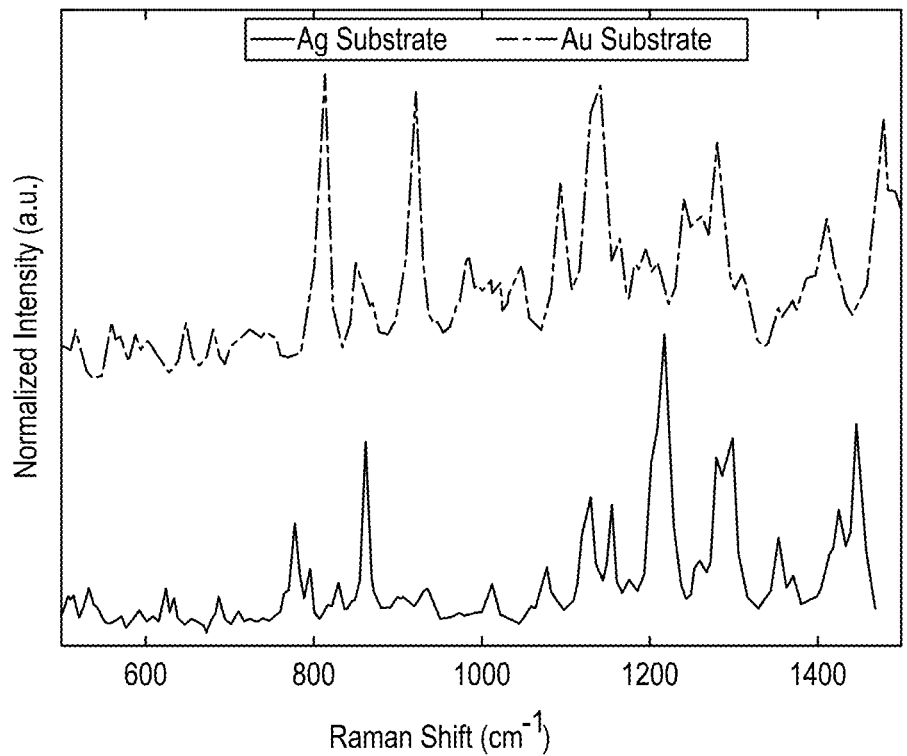

The component spectra associated with the GFP gene on a silver and gold substrate are shown in FIG. 8D. These component spectra show many spectral differences, only sharing 3 peaks with the same frequencies but differing intensities. The peaks are 1260, 1281, and 1354 cm$^{-1}$ corresponding to the amide III stretch (Ashton et al., "pH-Induced Conformational Transitions in α-Lactalbumin Investigated with Two-Dimensional Raman Correlation Variance Plots and Moving Windows," *Journal of Molecular Structure* 974(1-3):132-138 (2010), which is hereby incorporated by reference in its entirety), arginine (Negri et al., "Online SERS Detection of the 20 Proteinogenic 1-Amino Acids Separated by Capillary Zone Electrophoresis," *The Analyst* 139(22):5989-5998 (2014), which is hereby incorporated by reference in its entirety), and tryptophan (Ashton et al., "pH-Induced Conformational Transitions in α-Lactalbumin Investigated with Two-Dimensional Raman Correlation Variance Plots and Moving Windows," *Journal of Molecular Structure* 974(1-3):132-138 (2010), which is hereby incorporated by reference in its entirety) respectively. The full lists of peak assignments are shown in Tables 1 and 2. The spectrum on a silver substrate shows more bands associated with nucleic acids than amino acids compared to the gold substrates.

TABLE 2

Peak Assignments for Component 3 Loading
Spectrum of the MCR Model Created Using
SERS Spectra Acquired on Silver Substrates

| SERS Band (cm$^{-1}$) | Peak Assignments |
| --- | --- |
| 623 | Guanine |
| 632 | Tyrosine |
| 687 | Adenine |
| 709 | Cytosine |
| 777 | Cytosine/Uracil |
| 794 | Cytosine |
| 830 | Tyrosine |
| 862 | Tyrosine |
| 907 | Uracil |
| 1012 | Tryptophan |
| 1077 | Threonine |
| 1128 | Adenine |
| 1155 | Guanine |
| 1178 | Ribose Phosphate |
| 1217 | Uracil |
| 1260 | Amide III |
| 1281 | Arginine |
| 1298 | Uracil |
| 1354 | Tryptophan |
| 1427 | Cytosine |
| 1447 | CH$_2$ deformation of proteins |

Discussion of Examples 1 and 2

The results show that SERS is capable of detecting and quantifying a single type of virus particles that only differ by the insertion of a GFP gene. These results provide a significantly more rapid method of quantifying virus particles successfully transformed to encode a specific gene with less sample preparation than existing techniques. The quantification of these particles depends on the virus particles interacting with a hotspot on the surface of the SERS active substrate. Since the spectra observed depend on the orientation and specific parts of the virus interacting with a hotspot, quantification can be difficult to achieve using a single peak. MCR is shown to be useful for quantification of these complex signals by decomposing the SERS spectra into components, so that the scores can be used to determine the amount of virus present. Functionalizing the substrate surface could also be explored to force a specific orientation of the virus to improve the uniformity of the signals.

The signals associated with the particles containing the GFP gene are different depending on the excitation wavelength and metal used for the SERS substrate. When using a 532 nm excitation laser and a silver substrate, more of the peaks are associated with nucleic acids compared to the spectra using 785 nm excitation and a gold substrate. Previous studies of SERS on virus particles have used silver substrates with 785 nm excitation show that both nucleic acids and amino acids can be detected (Shanmukh et al., "Rapid and Sensitive Detection of Respiratory Virus Molecular Signatures Using a Silver Nanorod Array SERS Substrate," *Nano Letters* 6(11):2630-2636 (2006), which is hereby incorporated by reference in its entirety). However, a study using gold substrates with 785 nm excitation show that most of the SERS signal arises from amino acid and lipid components of the virus envelope (Lim et al., "Identification of Newly Emerging Influenza Viruses by Surface-Enhanced Raman Spectroscopy," *Analytical Chemistry* 87(23):11652-11659 (2015), which is hereby incorporated by reference in its entirety). The component spectrum of the virus with GFP on silver substrates show more nucleic acid signals than those on gold substrates. However, nucleic acid and amino acid signals are observed with both types of substrates.

The interaction between the metal and analyte can also affect how the molecule adsorbs to the surface, which will thus affect the observed SERS signal. This can be due to a preferred orientation of the analyte onto the surface, which will cause the bands closest to the surface to become more enhanced than those further away from the substrate. The SERS spectra of red blood cells appear to be different when silver nanoparticles are used instead of gold, which is explained by differing interactions between the analyte and each metal (Drescher et al., "SERS Reveals the Specific Interaction of Silver and Gold Nanoparticles with Hemoglobin and Red Blood Cell Components," *Physical Chemistry Chemical Physics* 15:5364-5373 (2013), which is hereby incorporated by reference in its entirety). Similar effects are likely the cause for the different signals of the virus particles containing GFP on silver and gold substrates.

SERS provides a more rapid approach to determining viral titer with less sample preparation than current methods. SERS has already been shown to distinguish between virus types and strains (Shanmukh et al., "Rapid and Sensitive Detection of Respiratory Virus Molecular Signatures Using a Silver Nanorod Array SERS Substrate," *Nano Letters* 6(11):2630-2636 (2006); Lim et al., "Identification of Newly Emerging Influenza Viruses by Surface-Enhanced Raman Spectroscopy," *Analytical Chemistry* 87(23):11652-11659 (2015), which are hereby incorporated by reference in their entirety) as well as using a DNA hairpin for detecting viral mutations (Dardir et., "SERS Nanoprobe for Intracellular Monitoring of Viral Mutations," *The Journal of Physical Chemistry C* 124(5):3211-3217 (2020), which is hereby incorporated by reference in its entirety). The methods described in the present application for the determination of viral titer using direct SERS measurements and can be applied to other virus types. This may also be used to quantify modifications to a viral genome.

Conclusion

As demonstrated in the preceding examples, the viral titer can be determined without modifications to the SERS substrate, thus providing a rapid and straightforward method using commercially available SERS substrates. Due to the complexity of the virus particle structure, a chemometric analysis, e.g., MCR, is useful to decompose the spectra so that a virus-specific component can be determined and used for quantification. The viral titers used in the preceding examples are an order of magnitude lower than those that are commonly used in biomedical applications. The use of different metals and excitation wavelengths for analyzing these particles was also studied, and showed that silver substrates with 532 nm excitation produced spectra with more nucleic acid features than gold substrates with 785 nm excitation. SERS provides a rapid method of determining viral titer with minimal sample preparation, and these results confirm that this method can be applied to various types of viruses.

Figure 9:
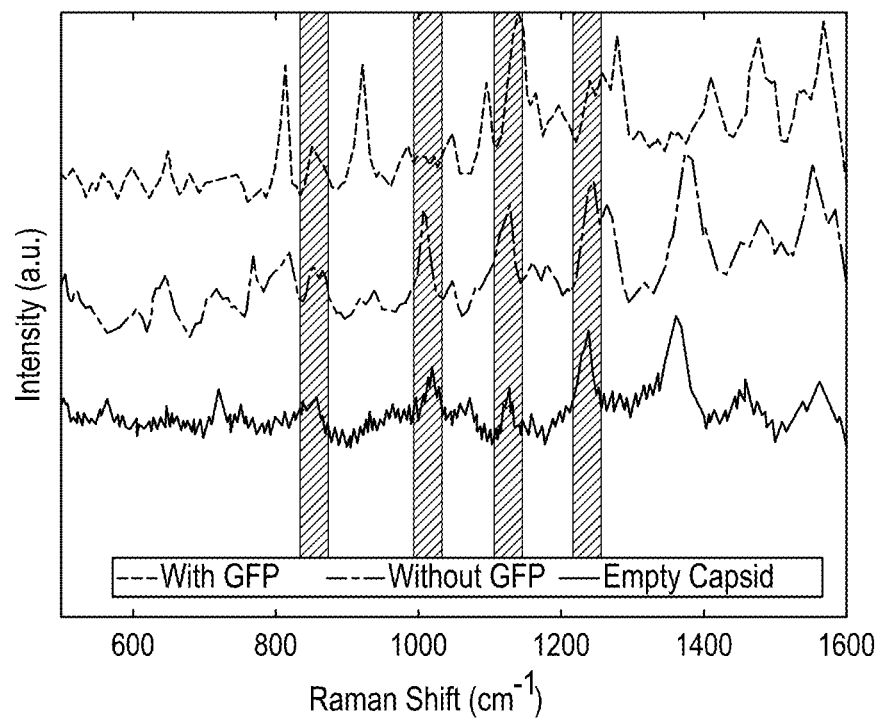
FIG. 9 is a graph showing SERS spectra collected from lentivirus particles encoding for GFP (top), identical but without the GFP gene (middle), and from a lentivirus particle without RNA within the capsid (empty capsid, bottom). Spectroscopic differences are observed that can be correlated with genetic contents present in the virus. All spectra collected using 785 nm excitation with gold SERS substrates.

Example 3: Detecting and Distinguishing Between Full and Empty Lentivirus Capsids SERS spectra were acquired using 785 nm excitation with gold SERS substrates for the analysis of lentiviruses containing either a full or empty lentiviral capsid. Commercially available lentiviruses (LentiArray CRISPR Negative Control Lentivirus, human non-targeting with green Fluorescent protein (GFP) and without GFP) were purchased from ThermoFisher Scientific and gold SERS substrates were purchased from Silmeco for full lentivirus measurements. Empty capsid lentivirus was purchased from SignaGen. Thermally evaporated gold substrates were produced using a previously described procedure and used for empty capsid experiments (Asiala et al., "Characterization of Hotspots in a Highly Enhancing SERS Substrate," *Analyst* 136(21): 4472-4479 (2011), which is hereby incorporated by reference in its entirety). A homebuilt Raman instrument was used to perform Raman spectroscopy by focusing the laser onto the SERS substrate through a 40×water immersion objective (NA=0.8). The Raman scattering was directed to an Isoplane SCT-320 spectrograph with a ProEM: $1600^2$ eXcelon 3 CCD detector (Princeton Instruments). The virus solutions were injected onto the SERS substrate and spectra were acquired with an exposure time of 250 ms and a laser power of 1.50 mW for full lentivirus and an exposure time of 500 ms with a laser power of 0.50 mW for empty lentivirus. The spectra shown in FIG. 9 are averages of 720 spectra. The differences in the SERS signals between the full and empty virus particles can be associated with the absence of genetic material within the capsid. The peaks highlighted by the gray boxes are seen across all 3 virus particles (Table 3) and correspond to tyrosine (853 $cm^{-1}$), phenylalanine (1004 $cm^{-1}$), tryptophan (1127 $cm^{-1}$), and the Amide III stretch (1240 $cm^{-1}$) (Shanmukh et al., "Rapid and Sensitive Detection of Respiratory Virus Molecular Signatures Using a Silver Nanorod Array SERS Substrate," *Nano Letters* 6(11):2630-2636 (2006); Ashton et al., "pH-Induced Conformational Transitions in α-Lactalbumin Investigated with Two-Dimensional Raman Correlation Variance Plots and Moving Windows," *Journal of Molecular Structure* 974(1-3):132-138 (2010); Verduin et al., "RNA-Protein Interactions and Secondary Structures of Cowpea Chlorotic Mottle Virus for in Vitro Assembly," *Biochemistry* 23(19):4301-4308 (1984), which are hereby incorporated by reference in their entirety). The additional bands seen in the empty capsid spectra (Table 4) include 719 $cm^{-1}$ (v(C-S), tryptophan), 1362 $cm^{-1}$ (tryptophan), 1454 $cm^{-1}$ ($CH_2$ deformation of proteins, tryptophan), and 1565 $cm^{-1}$ (Phenylalanine/tryptophan, Amide II) (Shanmukh et al., "Rapid and Sensitive Detection of Respiratory Virus Molecular Signatures Using a Silver Nanorod Array SERS Substrate," *Nano Letters* 6(11):2630-2636 (2006); Ashton et al., "pH-Induced Conformational Transitions in α-Lactalbumin Investigated with Two-Dimensional Raman Correlation Variance Plots and Moving Windows," *Journal of Molecular Structure* 974(1-3):132-138 (2010); Verduin et al., "RNA-Protein Interactions and Secondary Structures of Cowpea Chlorotic Mottle Virus for in Vitro Assembly," *Biochemistry* 23(19):4301-4308 (1984); Negri et al., "Online SERS Detection of the 20 Proteinogenic L-Amino Acids Separated by Capillary Zone Electrophoresis," *The Analyst* 139(22):5989-5998 (2014); Szekeres et al., "SERS Probing of Proteins in Gold Nanoparticle Agglomerates," *Front. Chem.* 7:30 (2019), which are hereby incorporated by reference in their entirety). The differences between the full and empty capsid spectra can be associated with the presence of genetic material within the virus, such as the bands at 812 cm$^{-1}$ arising from the phosphate backbone stretch of RNA, 921 cm$^{-1}$ arising from adenine, and 1046 cm$^{-1}$ arising from cytosine (Shanmukh et al., "Rapid and Sensitive Detection of Respiratory Virus Molecular Signatures Using a Silver Nanorod Array SERS Substrate," *Nano Letters* 6(11):2630-2636 (2006); Negri et al., "Detection of Genetic Markers Related to High Pathogenicity in Influenza by SERS," *The Analyst* 138(17):4877-4884 (2013); Suh et al., "Surface-Enhanced Raman Spectroscopy of Amino Acids and Nucleotide Bases Adsorbed on Silver," *Journal of the American Chemical Society* 108(16): 4711-4718 (1986), which are hereby incorporated by reference in their entirety).

TABLE 3

Shared Peaks Between Empty and Full Capsid

| SERS Band (cm$^{-1}$) | Assignments |
|---|---|
| 853 | Tyrosine |
| 1004 | Phenylalanine |
| 1127 | Tryptophan |
| 1240 | Amide III |

TABLE 4

Empty Capsid Peak Assignments

| SERS Band (cm$^{-1}$) | Assignments |
|---|---|
| 719 | ν(C—S), Tryptophan |
| 853 | Tyrosine |
| 1004 | Phenylalanine |
| 1127 | Tryptophan |
| 1240 | Amide III |
| 1362 | Tryptophan |
| 1454 | CH$_2$ deformation of proteins, Tryptophan |
| 1565 | Phenylalanine/Tryptophan, Amide II |

Example 4: Developing Calibration Curve for Modified Lentivirus Particles

Figure 10A:
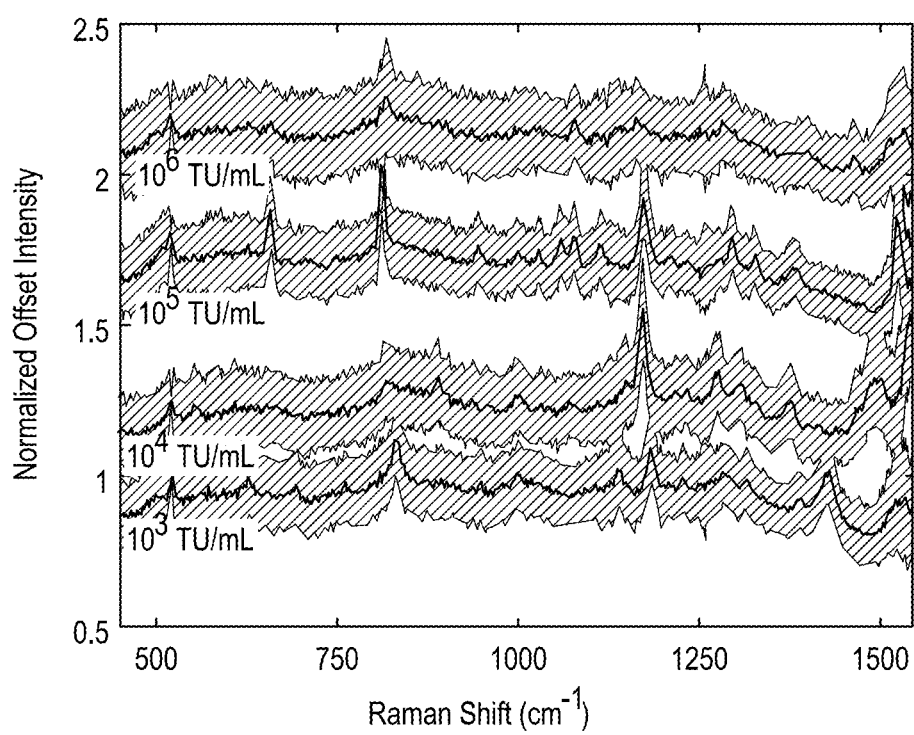
FIGS. 10A-10H show an MCR model for evaluation of modified lentivirus particles designated as JLV1.
Figure 10B:
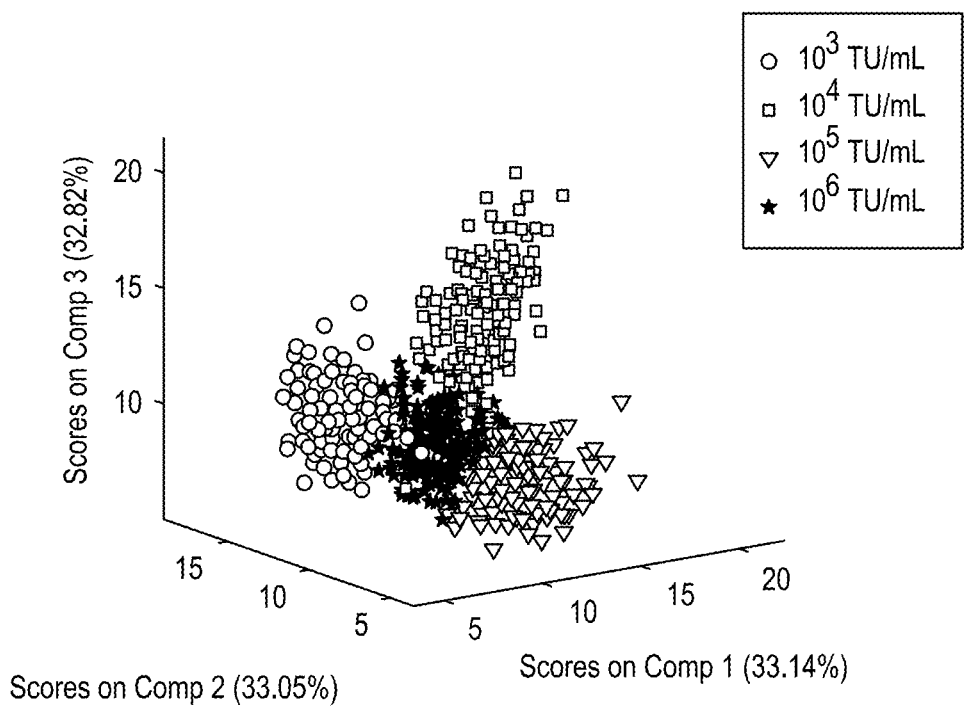
Figure 10C:
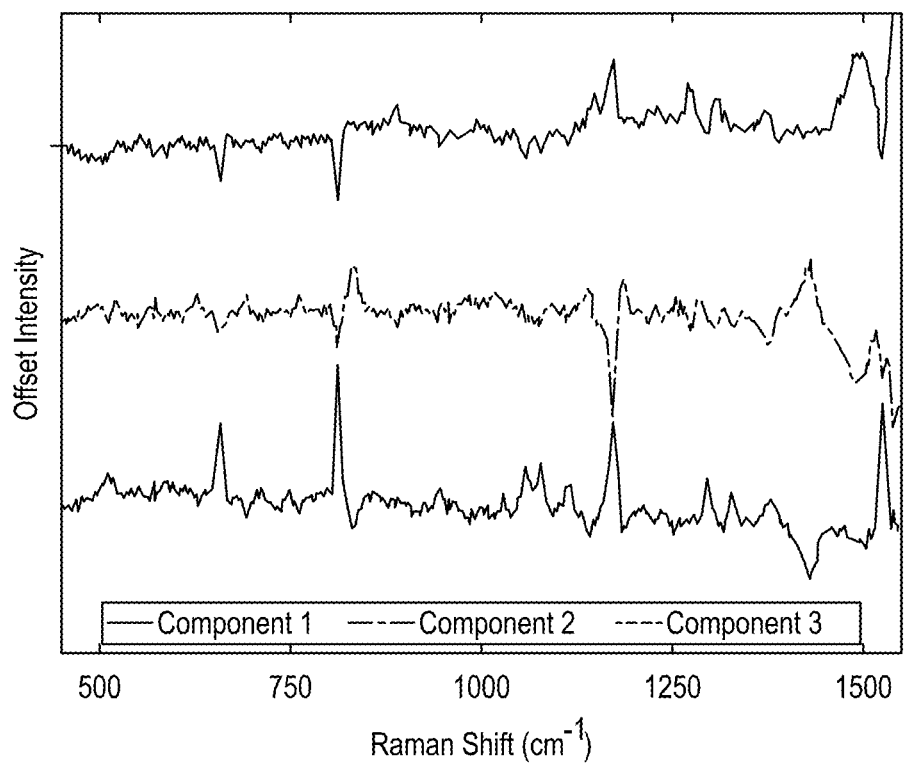
Figure 10D:
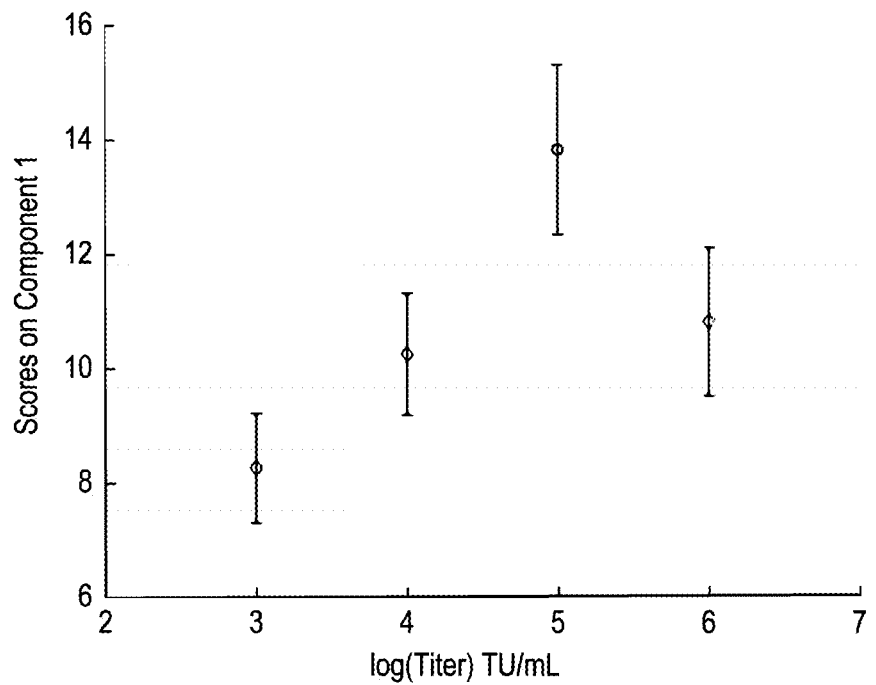
Figure 10E:
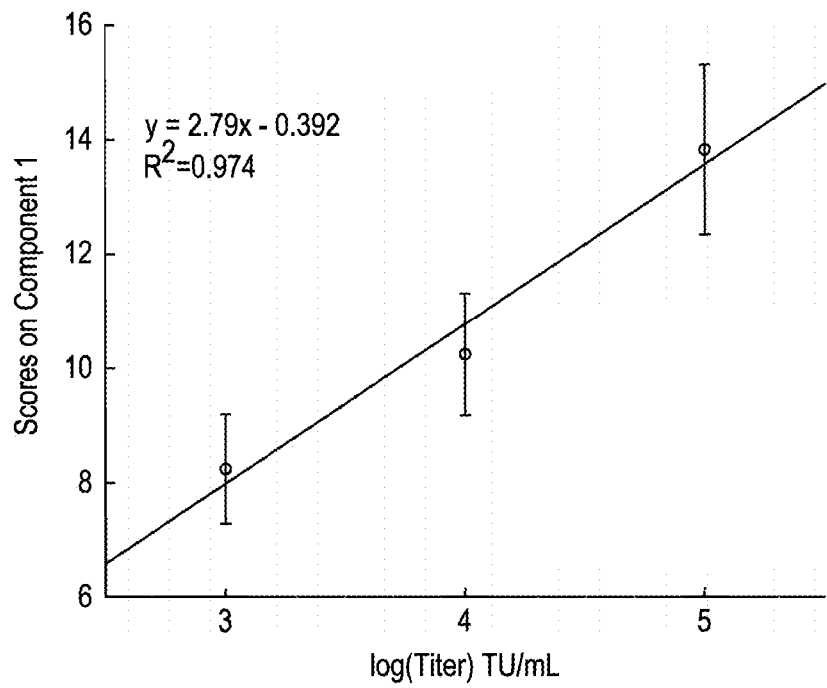
Figure 10F:
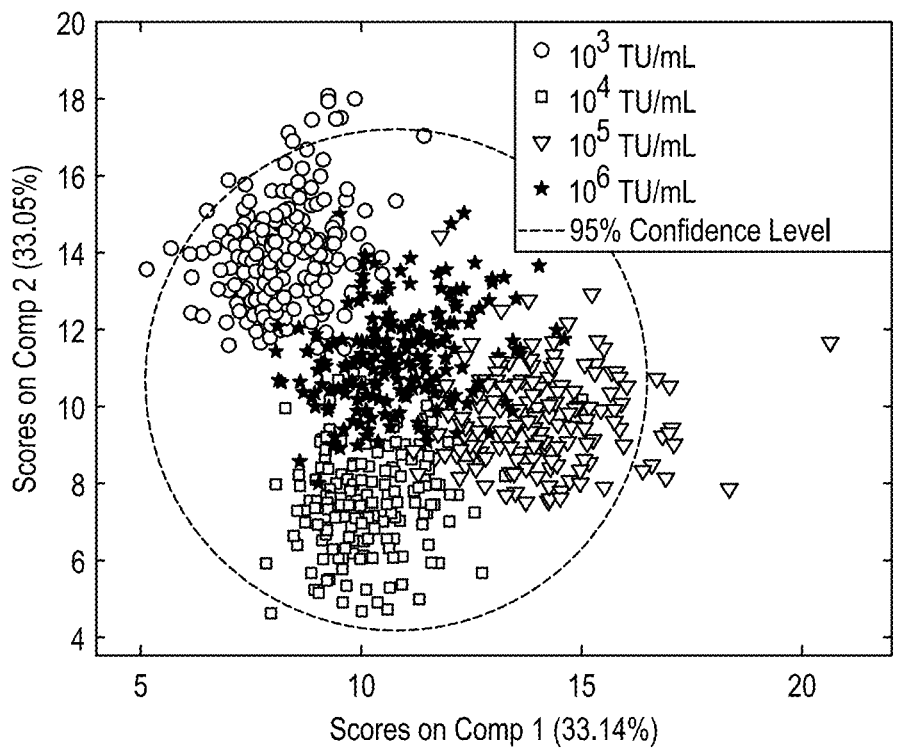
Figure 10G:
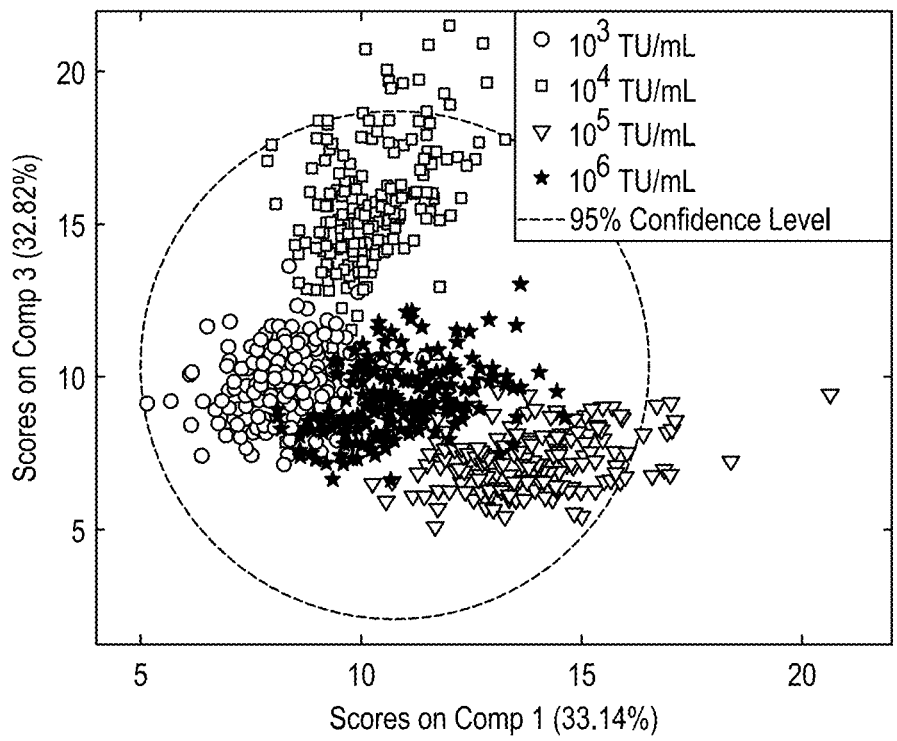
Figure 10H:
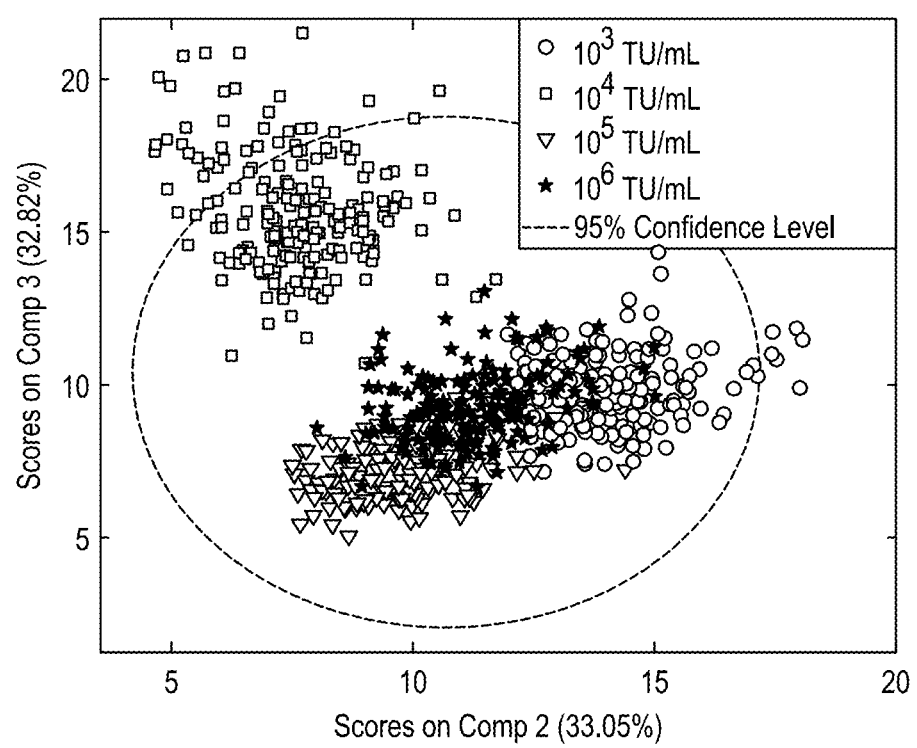

SERS spectra of modified lentivirus particles, designated JLV1, were acquired using a Snowy Range Sierra Raman Spectrometer with 638 nm excitation and commercial gold SERS substrates (Silmeco). The virus solutions were injected onto the SERS substrate through a 3D printed flow cell and spectra were acquired with an exposure time of 250 ms and a laser power of 0.50 mW. The spectra shown in FIG. 10A are averages of 200 spectra. All spectra were normalized to the 520 cm$^{-1}$ peak arising from the silicon backing of the SERS substrate prior to analysis. MCR was used to build a calibration model for determining viral titer, as shown in FIGS. 10B and 10C, and FIGS. 10F-H (comparing scores for components 1, 2, and 3). FIG. 10C shows the component 1 loading spectrum of this model having peaks arising from the amino acids and nucleic acids that makeup the virus, such as guanine (658 and 1380 cm$^{-1}$), phosphate backbone of RNA (811 and 1173 cm$^{-1}$), uracil (1059 and 1296 cm$^{-1}$), adenine (1328 cm$^{-1}$), and tryptophan (1115, 1380, and 1524 cm$^{-1}$) (Shanmukh et al., "Rapid and Sensitive Detection of Respiratory Virus Molecular Signatures Using a Silver Nanorod Array SERS Substrate," *Nano Letters* 6(11):2630-2636 (2006); Otto et al., "Surface-Enhanced Raman Spectroscopy of DNA Bases," *Journal of Raman Spectroscopy* 17(3):289-298 (1986); Suh et al., "Surface-Enhanced Raman Spectroscopy of Amino Acids and Nucleotide Bases Adsorbed on Silver," *Journal of the American Chemical Society* 108(16):4711-4718 (1986); Sloan-Dennison et al., "Surface Enhanced Raman Scattering Selectivity in Proteins Arises from Electron Capture and Resonant Enhancement of Radical Species," *The Journal of Physical Chemistry C* 124(17):9548-9558 (2020); Verduin et al., "RNA-Protein Interactions and Secondary Structures of Cowpea Chlorotic Mottle Virus for in Vitro Assembly," *Biochemistry* 23(19):4301-4308 (1984), which are hereby incorporated by reference in their entirety). The peaks that appear strongly in the loading spectrum also appear strongly in the average spectra for each titer as well, confirming that this component is associated with the lentiviral particles. The average score for each sample on component 1 was then plotted against viral titer (see FIGS. 10D-E) to develop a calibration curve. At the highest titer analyzed, 10$^6$ TU/mL, the SERS signal decreases (FIG. 10D). This is likely due to the surface being saturated with sample, thus blocking the additional lentivirus particles from occupying a hotspot and some of the SERS signal observed. However, below that titer level there is a linear trend between score on component 1 and viral titer, which was used to develop a calibration for determining viral titer of JLV1 shown in FIG. 10E ($R^2$=0.974). The error bars represent the standard deviations of the SERS measurements.

Based on the foregoing, the calibration curve can be used with the same set-up to assess virus titers below 10$^5$ TU/mL without sample dilution, and optionally at higher virus titers with a predetermined sample dilution (e.g., 10-fold, 100-fold, or greater). Both diluted and undiluted samples can optionally be evaluated in parallel.

Although preferred embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed is:

1. A method of quantifying viral titer in a sample using surface enhanced Raman spectroscopy (SERS), said method comprising:
   providing a sample containing a first virus particle and a second virus particle, wherein the first virus particle differs from the second virus particle by one or more genetic elements;
   providing a pre-trained, virus-type specific model for determining viral titer of the first virus particle in the sample;
   irradiating the sample with a light source;

acquiring a SERS spectrum of the sample on a gold or silver substrate, wherein the gold or silver substrate does not contain surface-bound reagents that promote virus particle binding; and quantifying the viral titer of the first virus particle in the sample by applying a virus-specific spectral component of the SERS spectrum associated with the one or more genetic elements of the first virus particle to the model for determining viral titer.

2. The method of claim 1, wherein the sample comprises two or more virus particles that differ by one or more genetic elements selected from gene insertions, substitutions, deletions, or translocations.

3. The method of claim 2, wherein the one or more genetic elements comprise an exogenous gene insertion into the virus particle genome.

4. The method of claim 2, wherein the virus particle is selected from a retrovirus particle, a retrovirus-like particle, an adenovirus particle, an adenovirus-like particle, an adeno-associated virus particle, an adeno-associated virus-like particle, a herpes simplex virus particle, and a herpes simplex virus-like particle.

5. The method of claim 2, wherein the virus particle is a lentivirus particle.

6. The method of claim 1, wherein the light source is a narrow bandwidth laser with a wavelength between 532-785 nm.

7. The method of claim 1, wherein the light source is a narrow bandwidth laser with a wavelength between 400-1064 nm.

8. The method of claim 1 further comprising:
extracting a score for the virus-specific spectral component from the SERS spectrum; and
applying the extracted score from the SERS spectrum of the sample to the model to quantify the viral titer in the sample;
wherein the model is a virus particle type-specific calibration curve, and a score for a virus particle type-specific spectral component is extracted and applied to the model to quantify a virus particle type-specific titer in the sample.

9. The method of claim 1, wherein the gold or silver substrate comprises nanostructures selected from nanorods, nanowires, nanotubes, nanospheres, or nanotriangles to enhance the SERS signal.

10. The method of claim 1, further comprising performing chemometric analysis selected from multivariate curve resolution (MCR), principal component analysis (PCA), or partial least squares (PLS) regression to extract virus-specific spectral components from the acquired SERS spectra, wherein the extracted spectral component is associated with the one or more genetic elements.

11. The method of claim 10, wherein the MCR is used to differentiate spectral components of first virus particles from culture medium, host cell debris, and process-related impurities, and wherein the virus-specific spectral component is applied to a pre-determined calibration curve to quantify viral titer of the first virus particles.

12. The method of claim 1, wherein the one or more genetic elements is an exogenous gene inserted into the viral genome of the first viral particles, and said quantifying distinguishes between first viral particles and second viral particles lacking the exogenous gene using a spectral marker associated with the exogenous gene which spectral marker is identified via chemometric analysis and validated against an independent method selected from ELISA, PCR, or flow cytometry.

13. A method for generating a model suitable for quantifying viral titer in a sample, said method comprising:
providing two or more samples, each sample containing a known virus type and known titer, wherein the known virus type in one sample comprises one or more genetic elements that are not present in the other virus types;
depositing each of the two or more samples on a gold or silver substrate, wherein the gold or silver substrate does not contain surface-bound reagents that promote virus particle binding, and subjecting each sample to surface enhanced Raman spectroscopy (SERS) to produce a reference spectrum for each known virus type and titer;
identifying a virus type-specific spectral component associated with the one or more genetic elements from the reference spectra;
determining a score for said component for each sample of known virus type and known titer; and
generating the model for quantifying viral titer based on said scores.

14. The method of claim 13, wherein said reference spectrum for each sample is produced by analyzing two or more spectra of said sample.

15. The method of claim 13 further comprising:
subtracting background spectrum from the reference spectrum prior to said identifying.

16. The method of claim 13, wherein said identifying comprises:
applying a chemometric analysis to the reference spectra produced from the two or more samples to identify one or more components of variation between the reference spectra;
assessing scores of the identified one or more components in spectra from two or more samples of each known virus type having different known titers; and
selecting, based on said assessing, the component correlating with known virus titer as the virus type-specific component.

17. The method of claim 16, wherein the chemometric analysis is a multivariate curve analysis.

18. The method of claim 13, wherein the generated model is a virus type-specific calibration curve.

19. The method of claim 13, wherein the one or more unique genetic elements are selected from gene insertions, substitutions, deletions, or translocations.

20. The method of claim 19, wherein the one or more genetic element comprises an exogenous gene insertion into the virus genome.

21. The method of claim 13, wherein the virus is selected from a retrovirus particle, a retrovirus-like particle, an adenovirus particle, an adenovirus-like particle, an adeno-associated virus particle, an adeno-associated virus-like particle, a herpes simplex virus particle, and a herpes simplex virus-like particle.

22. The method of claim 13, wherein the virus particle is a lentivirus particle.

23. The method of claim 13, wherein said subjecting comprises irradiating each sample with a narrow bandwidth laser with a wavelength between 532-785 nm.

24. The method of claim 23, wherein said subjecting further comprises acquiring the spectra with an exposure time of about 250 ms and about 1.50 mW.

25. The method of claim 13, wherein said subjecting comprises irradiating each sample with a narrow bandwidth laser with a wavelength between 400-1064 nm.

26. The method of claim 25, wherein said subjecting further comprises acquiring the spectra with an exposure time of about 250 ms and about 0.6 mW.

* * * * *